(12) United States Patent
Heller et al.

(10) Patent No.: US 8,940,866 B2
(45) Date of Patent: Jan. 27, 2015

(54) DETECTION OF DEGRADATIVE ENZYMES AND BIOMOLECULES IN BODILY FLUIDS

(71) Applicant: The Regents of the University of California, Oakland, CA (US)

(72) Inventors: Michael Heller, San Diego, CA (US); Geert W. Schmid-Schoenbein, Del Mar, CA (US); Roy B. Lefkowitz, La Jolla, CA (US); Benjamin Sullivan, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/936,882

(22) Filed: Jul. 8, 2013

(65) Prior Publication Data

US 2013/0281660 A1    Oct. 24, 2013

Related U.S. Application Data

(62) Division of application No. 12/866,732, filed as application No. PCT/US2009/033584 on Feb. 9, 2009, now Pat. No. 8,507,218.

(60) Provisional application No. 61/027,308, filed on Feb. 8, 2008.

(51) Int. Cl.
| | |
|---|---|
| *C07K 7/06* | (2006.01) |
| *C07K 7/08* | (2006.01) |
| *C12Q 1/34* | (2006.01) |
| *C12Q 1/37* | (2006.01) |
| *G01N 33/53* | (2006.01) |
| *C07K 5/103* | (2006.01) |

(52) U.S. Cl.
CPC ... *C07K 7/08* (2013.01); *C12Q 1/34* (2013.01); *C12Q 1/37* (2013.01); *G01N 33/53* (2013.01); *C07K 5/1008* (2013.01); *C07K 7/06* (2013.01)
USPC ........................................................ 530/327

(58) Field of Classification Search
CPC ........... C07K 5/1008; C07K 7/08; C07K 7/06
USPC ........................................................ 530/327
See application file for complete search history.

(56) References Cited

U.S. PATENT DOCUMENTS

| | | | |
|---|---|---|---|
| 5,580,747 A | 12/1996 | Shultz et al. | |
| 6,942,778 B1 | 9/2005 | Jalali et al. | |
| 7,326,326 B2 | 2/2008 | Chang et al. | |
| 2002/0123068 A1 | 9/2002 | Dwyer et al. | |
| 2003/0013098 A1 | 1/2003 | Brow et al. | |
| 2005/0055737 A1* | 3/2005 | Lough et al. | 800/278 |
| 2005/0173247 A1 | 8/2005 | Jalali et al. | |
| 2006/0210994 A1 | 9/2006 | Joyce | |
| 2011/0214199 A1* | 9/2011 | Coffin | 800/275 |
| 2013/0121915 A1* | 5/2013 | Paas et al. | 424/9.1 |

OTHER PUBLICATIONS

Anderson et al., "New Colorimetric Method for the Detection and Quantitation of Proteolytic Enzyme Activity", Journal of Agricultural and Food Chemistry, 1995, 43:1530-1534.
Delmar et al., "A Sensitive New Substrate for Chymotrypsin[1]", Analytical Biochemistry, 1979, 99:316-320.
Heller et al., "Lab-on-Chip device for rapid detection of Thrombin and other Protease activities directly in whole blood samples", Biosensors & Bioelectronics, 2012, 2(4)87.
International Preliminary Report on Patentability and Written Opinion dated Aug. 10, 2010 for International Application No. PCT/US2009/033584, 4 pages.
International Search Report dated Sep. 5, 2009 for International Application No. PCT/US2009/033584, 4 pages.
Jones et al., "Quenched BODIPY Dye-Labeled Casein Substrates for the Assay of Protease Activity by Direct Fluorescence Measurement", Analytical Biochemistry, 1997, 251:144-152.
Kleiner et al., "Quantitative Zymography: Detection of Picogram Quantities of Gelatinases", Analytical Biochemistry, 1994, 218:325-329.
Levine et al., "Measurement of a Specific Protease Activity Utilizing Fluorescence Polarization", Analytical Biochemistry, 1997, 247:83-88.
Schade et al., "BODIPY-α-Casein, a pH-Independent Protein Substrate for Protease Assays Using Fluorescence Polarization[1]", Analytical Biochemistry, 1996, 243:1-7.
Sinha, et al. "Demonstration of Protease Isoenzymes by Two Dimensional Polyacrylamide Electrophoresis." Histochemistry, 1983, 79:483-486.
Stockholm et al., "Imaging Calpain Protease Activity by Multiphoton FRET in Living Mice", Journal of Molecular Biology, 2005, 346:215-222.
Zhang et al., "Detection of Mitochondrial Caspase Activity in Real Time In Situ in Live Cells", Microscopy and Microanalysis, 2004, 10:442-448.
Zimmerman et al., "Sensitive Assays for Trypsin, Elastase, and Chymotrypsin Using New Fluorogenic Substrates", Analytical Biochemistry, 1977, 78:47-51.

* cited by examiner

*Primary Examiner* — Julie Ha
(74) *Attorney, Agent, or Firm* — Kilpatrick Townsend & Stockton LLP

(57) ABSTRACT

Provided herein are compositions useful in detecting degradative enzymes and biomolecules in bodily fluid samples.

5 Claims, 29 Drawing Sheets

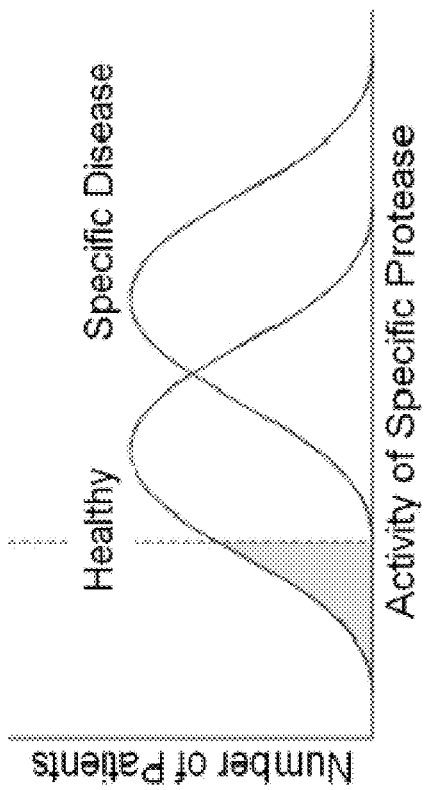
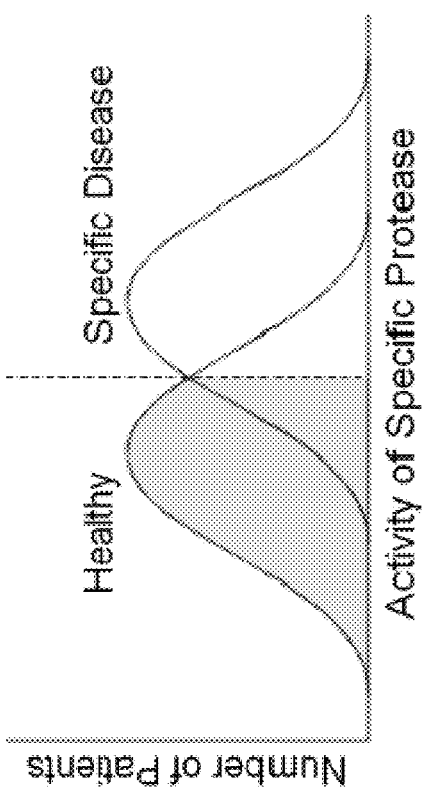
FIG. 1A
FIG. 1B

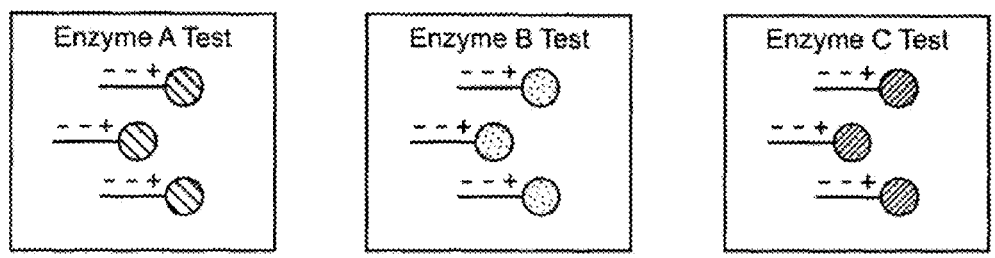
Add blood/plasma with unknown enzyme A, B, and C ???
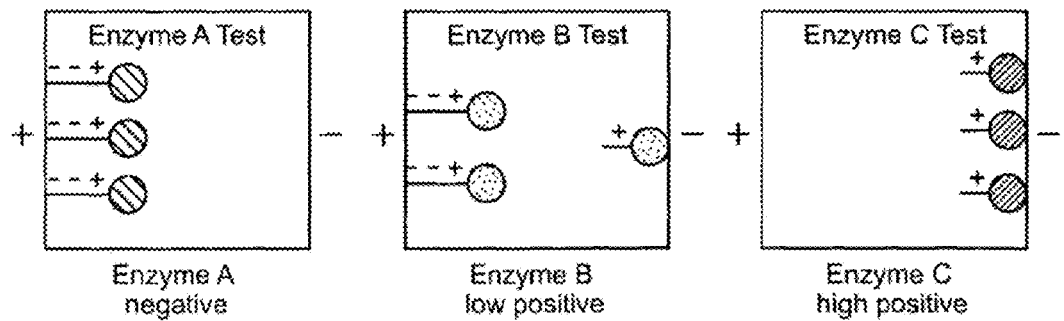
FIG. 6

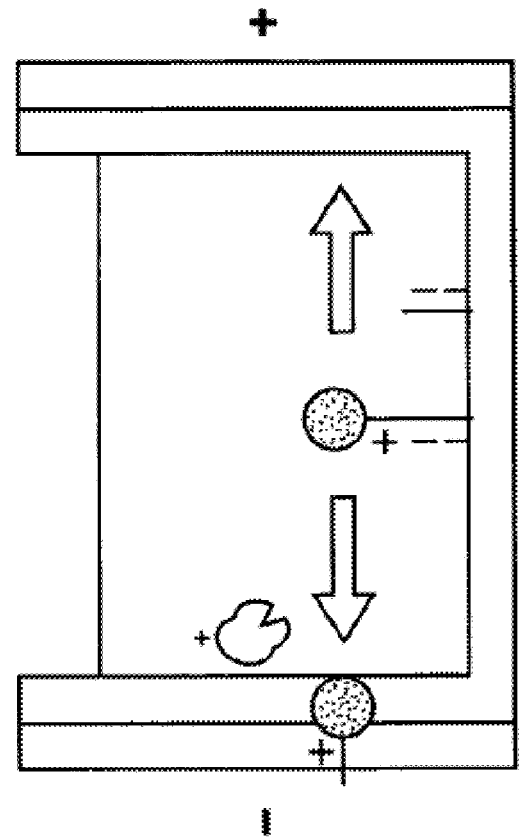
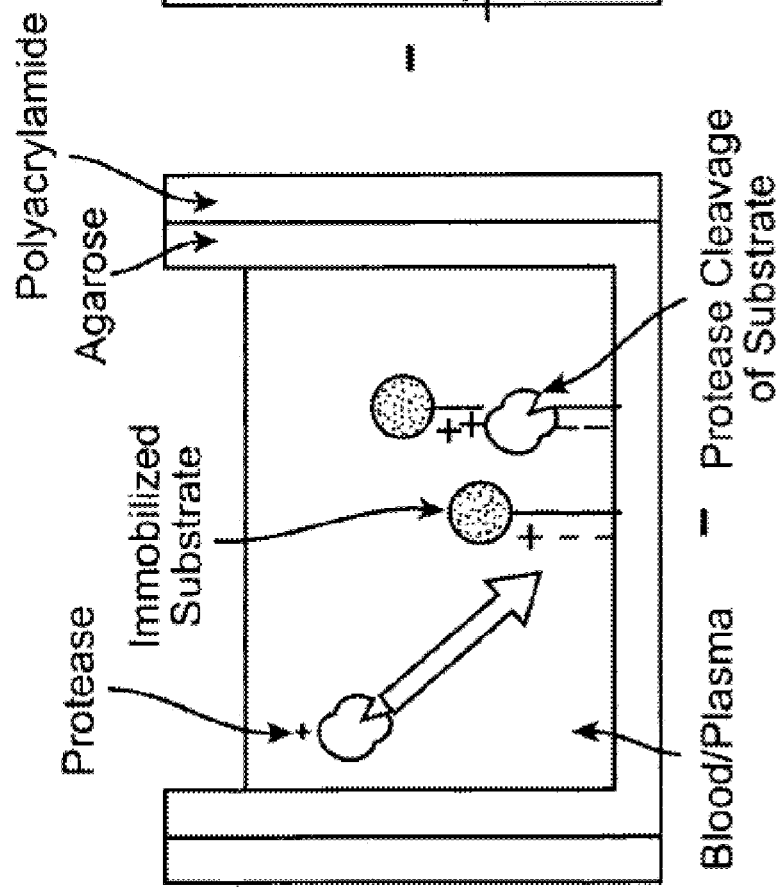
FIG. 18

```
                         SEQUENCE LISTING

<160> NUMBER OF SEQ ID NOS: 30

<210> SEQ ID NO 1
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1

Gly Asp Ala Gly Tyr Ala Gly Ala Gly Lys
1               5                   10

<210> SEQ ID NO 2
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 2

Asp Gly Asp Ala Gly Arg Ala Gly Ala Gly Lys
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 3

Asp Ala Gly Ser Val Ala Gly Ala Gly Lys
1               5                   10

<210> SEQ ID NO 4
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 4

Gly Asp Leu Ala Ala Ile Thr Ala Ala Gly Ala Gly Lys
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 5

Gly Asp Pro Val Gly Leu Thr Ala Gly Ala Gly Lys
1               5                   10

<210> SEQ ID NO 6
<211> LENGTH: 13
<212> TYPE: PRT
<213> ORGANISM: Artificial sequence
<220> FEATURE:
```

```
<223> OTHER INFORMATION: Synthetic polypeptide

<400> SEQUENCE: 6

Gly Asp Leu Ile Ser His Ser Ile Ala Gly Ala Gly Lys
1               5                   10

<210> SEQ ID NO 7
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 7

Asp Gly Asp Ala Gly Tyr Ala Gly Leu Arg Gly Ala Lys
1               5                   10

<210> SEQ ID NO 8
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
<220> FEATURE:
<221> NAME/KEY: MOD_RES
<222> LOCATION: (10)..(10)
<223> OTHER INFORMATION: Residue 10 modified at epsilon amino with
      Bodipy TR

<400> SEQUENCE: 8

Gly Asp Ala Gly Tyr Ala Gly Ala Gly Lys
1               5                   10

<210> SEQ ID NO 9
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: AMIDATION
<220> FEATURE:
<221> NAME/KEY: MOD_RES
<222> LOCATION: (11)..(11)
<223> OTHER INFORMATION: Residue 11 modified at epsilon amino with
      Bodipy TR

<400> SEQUENCE: 9

Asp Gly Asp Ala Gly Arg Ala Gly Ala Gly Lys
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
<220> FEATURE:
<221> NAME/KEY: MOD_RES
<222> LOCATION: (10)..(10)
<223> OTHER INFORMATION: Residue 10 modified at epsilon amino with
      Bodipy TR

<400> SEQUENCE: 10

Asp Ala Gly Ser Val Ala Gly Ala Gly Lys
1               5                   10

<210> SEQ ID NO 11
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION
<220> FEATURE:
<221> NAME/KEY: MOD_RES
<222> LOCATION: (13)..(13)
<223> OTHER INFORMATION: Residue 13 modified at epsilon amino with
      Bodipy TR

<400> SEQUENCE: 11

Gly Asp Leu Ala Ala Ile Thr Ala Ala Gly Ala Gly Lys
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION
<220> FEATURE:
<221> NAME/KEY: MOD_RES
<222> LOCATION: (12)..(12)
<223> OTHER INFORMATION: Residue 12 modified at epsilon amino with
      Bodipy TR

<400> SEQUENCE: 12

Gly Asp Pro Val Gly Leu Thr Ala Gly Ala Gly Lys
1               5                   10

<210> SEQ ID NO 13
<211> LENGTH: 13
<212> TYPE: PRT
<213> ORGANISM: Artificial sequence
<220> FEATURE:
<223> OTHER INFORMATION: Synthetic polypeptide
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION
<220> FEATURE:
<221> NAME/KEY: MOD_RES
<222> LOCATION: (13)..(13)
<223> OTHER INFORMATION: Residue 13 modified at epsilon amino with
      Bodipy TR

<400> SEQUENCE: 13

Gly Asp Leu Ile Ser His Ser Ile Ala Gly Ala Gly Lys
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION
<220> FEATURE:
<221> NAME/KEY: MOD_RES
<222> LOCATION: (13)..(13)
<223> OTHER INFORMATION: Residue 13 modified at epsilon amino with
      Bodipy TR

<400> SEQUENCE: 14

Asp Gly Asp Ala Gly Tyr Ala Gly Leu Arg Gly Ala Lys
1               5                   10

<210> SEQ ID NO 15
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified at N-terminal with PEG
      linker, which in turn is modified with N-Ac Asp
<220> FEATURE:
<221> NAME/KEY: MOD_RES
<222> LOCATION: (4)..(4)
<223> OTHER INFORMATION: Residue 4 modified at C-terminal with PEG
      linker, which in turn is modified with Bodipy TR

<400> SEQUENCE: 15

Gly Tyr Ala Gly
1

<210> SEQ ID NO 16
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified at N-terminal with PEG
      linker, which in turn is modified with N-Ac-Asp-Asp
```

```
<220> FEATURE:
<221> NAME/KEY: MOD_RES
<222> LOCATION: (4)..(4)
<223> OTHER INFORMATION: Residue 4 modified at C-terminal with PEG
      linker, which in turn is modified with Bodipy TR

<400> SEQUENCE: 16

Gly Arg Ala Gly
1

<210> SEQ ID NO 17
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: D-Asp
<220> FEATURE:
<221> NAME/KEY: MISC_FEATURE
<222> LOCATION: (3)..(3)
<223> OTHER INFORMATION: D-Ala
<220> FEATURE:
<221> NAME/KEY: MISC_FEATURE
<222> LOCATION: (8)..(8)
<223> OTHER INFORMATION: D-Ala
<220> FEATURE:
<221> NAME/KEY: MISC_FEATURE
<222> LOCATION: (10)..(10)
<223> OTHER INFORMATION: D-Lys
<220> FEATURE:
<221> NAME/KEY: MOD_RES
<222> LOCATION: (10)..(10)
<223> OTHER INFORMATION: AMIDATION
<220> FEATURE:
<221> NAME/KEY: MOD_RES
<222> LOCATION: (10)..(10)
<223> OTHER INFORMATION: Residue 10 modified at epsilon amino with
      Bodipy TR

<400> SEQUENCE: 17

Gly Asp Ala Gly Tyr Ala Gly Ala Gly Lys
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Asp
<220> FEATURE:
<221> NAME/KEY: MISC_FEATURE
<222> LOCATION: (3)..(3)
<223> OTHER INFORMATION: D-Asp
<220> FEATURE:
<221> NAME/KEY: MISC_FEATURE
<222> LOCATION: (4)..(4)
<223> OTHER INFORMATION: D-Ala
<220> FEATURE:
<221> NAME/KEY: MISC_FEATURE
<222> LOCATION: (9)..(9)
```

```
<223> OTHER INFORMATION: D-Ala
<220> FEATURE:
<221> NAME/KEY: MISC_FEATURE
<222> LOCATION: (11)..(11)
<223> OTHER INFORMATION: D-Lys
<220> FEATURE:
<221> NAME/KEY: MOD_RES
<222> LOCATION: (11)..(11)
<223> OTHER INFORMATION: AMIDATION
<220> FEATURE:
<221> NAME/KEY: MOD_RES
<222> LOCATION: (11)..(11)
<223> OTHER INFORMATION: Residue 11 modified at epsilon amino with
      Bodipy TR

<400> SEQUENCE: 18

Asp Gly Asp Ala Gly Arg Ala Gly Ala Gly Lys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION

<400> SEQUENCE: 19

Asp Gly Asp Ala Gly Tyr Ala Gly Lys Arg Gly Ala Gly
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION

<400> SEQUENCE: 20

Asp Gly Asp Ala Gly Tyr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 21

Ala Gly Leu Arg Gly Ala Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 22

Gly Glu Gly Ala Phe Gly Ala Arg Gly
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (9)..(9)
<223> OTHER INFORMATION: Residue 9 modified with biotin

<400> SEQUENCE: 23

Gly Glu Gly Ala Phe Gly Ala Arg Gly
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified with biotin which is further
      bound to streptavidin quantum dot
<220> FEATURE:
<221> NAME/KEY: MOD_RES
<222> LOCATION: (10)..(10)
<223> OTHER INFORMATION: AMIDATION

<400> SEQUENCE: 24

Gln His Trp Ser Tyr Gly Leu Arg Pro Gly
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: Residue 13 modified with Bodipy FL

<400> SEQUENCE: 25

Asp Gly Asp Ala Gly Tyr Ala Gly Leu Arg Gly Ala Gly
1               5                   10

<210> SEQ ID NO 26
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified at N-terminal with
      N-acetyl-Asp-PEG
<220> FEATURE:
<221> NAME/KEY: MOD_RES
<222> LOCATION: (4)..(4)
<223> OTHER INFORMATION: Residue 4 modified at C-terminal with
      PEG-Bodipy TR
```

```
<400> SEQUENCE: 26

Gly Tyr Ala Gly
1

<210> SEQ ID NO 27
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified at N-terminal with
      N-acetyl-Asp-Asp-PEG
<220> FEATURE:
<221> NAME/KEY: MOD_RES
<222> LOCATION: (4)..(4)
<223> OTHER INFORMATION: Residue 4 modified at C-terminal with
      PEG-Bodipy TR

<400> SEQUENCE: 27

Gly Arg Ala Gly
1

<210> SEQ ID NO 28
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (8)..(8)
<223> OTHER INFORMATION: Residue 8 modified with Bodipy TR

<400> SEQUENCE: 28

Asp Gly Ala Val Gly Ala Val Lys
1               5

<210> SEQ ID NO 29
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: Residue 13 modified at C-terminal with
      diamino-ethyl Bodipy FL

<400> SEQUENCE: 29

Asp Gly Asp Ala Gly Tyr Ala Gly Leu Arg Gly Ala Gly
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic polypeptide
```

```
<400> SEQUENCE: 30

Pro Glu Cys Pro Ser Gly Tyr Thr Met Asn Ser Ser
1               5                   10
```

DETECTION OF DEGRADATIVE ENZYMES AND BIOMOLECULES IN BODILY FLUIDS

CROSS-REFERENCES TO RELATED APPLICATIONS

This application is a divisional of U.S. patent application Ser. No. 12/866,732, filed Aug. 6, 2010, which is a U.S. National Stage of International Application No. PCT/US2009/033584, filed Feb. 9, 2009, which claims the benefit of U.S. Provisional Application No. 61/027,308, filed on Feb. 8, 2008, each of which is herein incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 88654-878917_ST25.TXT, created on Jul. 2, 2013, 11,158 bytes, machine format IBM-PC, MS-Windows operating system, is hereby incorporated by reference.

BACKGROUND OF THE INVENTION

Increasing evidence suggests that there is an association between an inflammatory cascade and physiological shock [1, 2], diabetes [3, 4], cardiovascular diseases [5-10], acute cerebral stroke [11-15], Alzheimer's chronic disease [16], and various other diseases. This cascade is accompanied by activation of cells, expression of pro-inflammatory genes, down regulation of anti-inflammatory genes, attachment of leukocytes to the endothelium, elevated permeability of the endothelium, thrombosis, mast cell degranulation, apoptosis, growth factor release, and other events [17]. This evidence has opened up great opportunities in medicine to develop a variety of new anti-inflammatory interventions in an increasing number of diseases. Recent research designed to determine the origin of the trigger mechanisms of the inflammatory cascade in shock, multi-organ failure, and other diseases show that there exists an enhanced level of degradative enzymes that are targeted towards a variety of autologous proteins, protein structures, lipids, and lipid structures [1, 18-20]. This enzyme activity is not blocked to the same level as in non-disease control samples.

In shock, for example, digestive enzymes (e.g. chymotrypsin, trypsin, elastase, lipase, nuclease) synthesized in the pancreas find entry into the wall of the intestine [1]. Physiological shock is a life-threatening cardiovascular complication with high mortality that occurs in situations associated with trauma, including burns, surgery, ischemia, and sepsis. These traumas cause a reduced blood flow in the intestine, which in turn triggers an increased epithelial and endothelial permeability. This allows pancreatic enzymes to enter systemic circulation via the portal vein and/or intestinal lymphatics, where they produce a chain of events, including the production of inflammatory mediators (toxic protein fragments), inflammation, self-digestion of tissues, multi-organ failure, and eventually death. These enzymes have the ability to degrade almost all biological tissues and molecules, and, when exposed to the body during shock, lead to auto-digestion of matrix proteins and tissue cells in the intestinal wall and to the production of inflammatory mediators, which in turn further enhances the level of inflammation. Detection of these proteases in the blood can therefore diagnose a patient for the early stages of physiological shock, as well as for chronic and acute inflammation. It is also believed that the detection of lipases, amylases, and nucleases may be important for diagnosing these diseases. Furthermore the detection of proteases, lipases, amylases, and nucleases may also be important for many other diseases, including heart disease and cancer i.e., pancreatic cancer in particular.

As an additional example, diabetes is a disease characterized by excessive blood glucose levels [21]. Too much glucose in the blood can cause acute complications such as hypoglycemia, ketoacidosis and nonketotic hyperosmolar coma, as well as chronic complications such as cardiovascular disease, chronic renal failure, retinal damage (potentially resulting in blindness), several types of nerve damage, and microvascular damage (which can lead to impotence and poor healing). Glucose uptake from the blood is stimulated by the hormone insulin. Diabetes occurs when this hormone can't be synthesized by the body (type I) or when the body has resistance or decreased sensitivity to it (type II). For the latter case, recent evidence has shown that one particular pathogenesis of this insulin resistance may be proteolytic cleavage of the extracellular α-subunit of the insulin receptor by matrix metalloproteases (MMPs) [22]. It was shown, that spontaneously hypertensive rats (SHR) had significantly elevated MMP-9 protein levels in SHR microvessels, and elevated levels of leukocytes compared to normotensive Wistar-Kyoto rats. Furthermore, in-vivo micro-zymography showed enhanced cleavage by MMP-1,9 that co-localized with MMP-9 and was blocked by metal chelation. Using an antibody against the extracellular domain of the insulin receptor, this study further showed reduced density of the insulin receptor-α and a corresponding elevation of glucose and glycated hemoglobin in the blood, compared to the normotensive control. Treating the SHR with a broad spectrum MMP inhibitor, doxycycline, reversed all of these aforementioned trends. In other studies by Lee [23] and by Derosa [24], it was shown that there were elevated MMP-2, 9 levels in diabetic patients versus healthy patients. Together, all of these results show that one or more MMPs may be responsible for cleavage of the insulin receptor-alpha and corresponding insulin resistance, which in turn leads to type-2 diabetes. Detecting these matrix metalloproteases can therefore diagnose a developing insulin resistance during the early stages of type 2 diabetes.

Previous protease detection substrates and devices have included Fluorogenic Substrates [27, 28], Chromogenic Substrates [25, 26], FRET-Based Substrates [29, 30], EnzChek Assays, Immunohistochemical Assays, Fluorescence Polarization [31, 32] and Zymography [33]. These are protease assays based on cleavage of specific short amino-acid sequences designed to detect specific protease activity. The existing protease detection kits are based on 96 well plates with relatively large sample size (0.1 to 0.3 ml) each and they are not generally designed to detect cleavage of specific proteases. In general, these substrates are FRET type peptides which when cleaved by the protease produce an enhanced fluorescent signal or change in the fluorescent emission wavelength. Fluorescent PepTag® substrates are separated by gel electrophoresis after hydrolysis [34, 35]. These assays do not allow the detection of proteases directly in blood, cannot be separated easily from blood and plasma components, and are not useful for clinical diagnostics.

Other devices, systems and substrates for the detection of protein kinases and proteases have been designed [36, 37], however they appear not to be useful for rapid clinical diagnostic applications for the reasons discussed above.

Since the discovery of the link between the inflammatory cascade and physiological shock, diabetes, and potentially numerous other diseases, there have not been any detection platforms developed that could perform multiplex measurements of the clinical levels of disease related enzymes directly in blood or plasma. Therefore, there is a clear need for the rapid and quantitative detection of key disease related enzymes in formats that utilize minimal sample size and sample preparation. The present invention addresses these and other needs in the art.

BRIEF SUMMARY OF THE INVENTION

Provided herein are methods, kits and compositions useful in detecting degradative enzymes and biomolecules in bodily fluid samples.

In one aspect, a method of detecting a degradative enzyme in a bodily fluid sample is provided. The method includes the step of contacting the bodily fluid sample with a negatively charged degradative enzyme substrate or neutral degradative enzyme substrate. The degradative enzyme is allowed to react with the negatively charged degradative enzyme substrate or neutral degradative enzyme substrate thereby forming a positively charged degradative enzyme product. The positively charged degradative enzyme product is electrophoretically separated from the negatively charged degradative enzyme substrate or neutral degradative enzyme substrate. The separated positively charged degradative enzyme product is detected thereby detecting the degradative enzyme in the bodily fluid sample.

In another aspect, a peptide sequence is provided including at least one of the sequences of SEQ ID NOs:1-18 or conservative amino acid substitutions thereof.

In another aspect, a kit for detecting a degradative enzyme in a crude bodily fluid sample is provided. The kit includes a negatively charged degradative enzyme substrate or neutral degradative enzyme substrate.

In another aspect, a method is provided for detecting a biomolecule in a bodily fluid sample. The method includes contacting a bodily fluid sample with a first detection antibody and a second positively charged antibody to form a detectable positively charged biomolecule conjugate. The detectable positively charged biomolecule conjugate is electrophoretically separated from negatively charged endogenous material present in the bodily fluid sample. The detectable positively charged biomolecule conjugate is detected thereby detecting the biomolecule in the fluid sample.

In another aspect, a method of detecting a nucleic acid in a bodily fluid sample is provided. The method includes the steps of contacting the bodily fluid sample with a first detection nucleic acid and a second positively charged nucleic acid to form a detectable positively charged nucleic acid conjugate. The detectable positively charged nucleic acid conjugate is electrophoretically separated from negatively charged endogenous material present in the bodily fluid sample. The detectable positively charged nucleic acid conjugate is detected thereby detecting the nucleic acid in the bodily fluid sample.

BRIEF DESCRIPTION OF THE DRAWINGS

FIGS. 1A-1B. Populations of healthy patients and those with a specific disease have Gaussian distributions of activity of a specific protease. FIG. 1A: A threshold is set in a diagnostic test to designate which range of activities will produce a positive result. FIG. 1B: If the threshold is set lower to increase sensitivity of detection, this will increase false positives and hence lower specificity.

(FIG. 3A) Chymotrypsin substrate labeled with a fluorophore and a net charge of −1. The fluorescently labeled cleavage product has a net charge of +2. (FIG. 3B) Without an electric field, uncleaved substrate (background) and cleaved product (signal) are unresolved. (FIG. 3C) After application of an electric field, the uncleaved substrate and fluorescently labeled cleavage product migrate in opposite directions. The fluorescently labeled cleavage product can be detected by a fluorescent detector. Sequences: Ac-N-Asp-Gly-Asp-Ala-Gly-Tyr-Ala-Gly-Leu-Arg-Gly-Ala-Gly (SEQ ID NO:19); Ac-N-Asp-Gly-Asp-Ala-Gly-Tyr (SEQ ID NO:20); Ala-Gly-Leu-Arg-Gly-Ala-Gly (SEQ ID NO:21).

FIG. 6. Multiplexing NCDPS.

FIG. 18. Schematic of an enzyme separation and detection system which accelerates the reaction of the protease with immobilized NCDPS substrates.

FIG. 26A (upper); FIG. 26B (lower).

DETAILED DESCRIPTION OF THE INVENTION

I. Introduction

Figure 2:
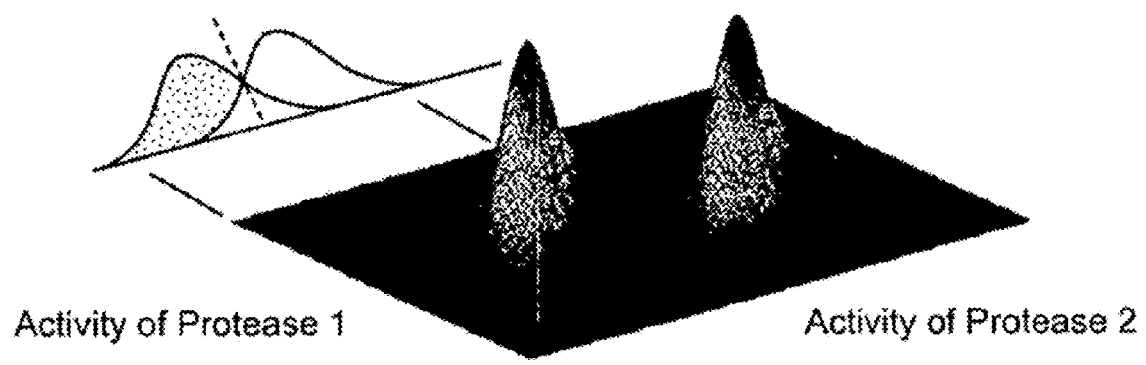
FIG. 2. A healthy and diseased population are not well resolved by the activity of a single protease (2D plot) but are better resolved by the activities of multiple proteases (3D plot).

Provided herein are, inter alia, methods for the design, synthesis and use of degradative enzyme substrates, such as net charge differentiating peptide substrates (NCDPS), for the rapid detection of disease related enzymes in bodily fluids such as blood, plasma and other biological samples. NCDPS's can be labeled with a variety of detection moieties which include but are not limited to organic fluorophores, quantum dots, fluorescent nanoparticles, fluorescent proteins, dendrimeric nanoparticles, and chemiluminescent and electrochemical labels. These NCDPS's can be used for the highly specific and sensitive detection of the key disease related enzymes, including but not limited to proteases, matrix metalloproteases, lipases, amylases, nucleases and protein kinases associated with shock, inflammatory responses and many other diseases. The substrates may be specifically designed for use in blood, plasma and other crude (e.g. un-processed) biological samples.

In some embodiments, the methods allow the rapid identification of specific disease related enzymes with little or no sample preparation. For example, upon cleavage by a specific enzyme, degradative enzyme substrates produce a cleavage product which has an overall net charge that is different from the original peptide substrate (e.g. neutral or negatively charged peptide substrates). The cleaved substrates (e.g. positively charged peptide substrates) may be specifically designed to be rapidly separated from the substrate itself, as well as components of a bodily fluid such as blood cells and other background blood and plasma components (hemoglobin, albumin, etc.). In certain embodiments, the substrate design allows the cleaved fluorescent peptide product fragments to be selectively concentrated by unique electrophoretic focusing/smart gels and microgel devices, as well as in microtiter plate and lab-on-a-chip devices providing greatly enhanced signal detection. Also provided are novel research and clinical diagnostic systems, devices and signal detection components which are synergistic with the NCDPS's, allowing the substrates to be used for the rapid detection of proteases and other enzymes directly in blood, plasma and other relevant samples.

In certain embodiments of the methods provided herein, electric fields are used to rapidly separate and concentrate fluorescent labeled peptide fragments after cleavage by a specific degradative enzyme. The process may be designed to greatly increase the sensitivity and specificity for detecting specific proteases and other enzyme (e.g. lipases, amylases, nucleases, kinases, etc.) directly in blood or plasma. Where low levels of the target degradative enzyme or biomolecules are present, highly sensitive and specific methods are required. In some embodiments, highly sensitive and specific methods are required for patient monitoring and point of care (POC) applications. Cleavage of degradative enzyme substrates results in a change in the net charge on the complex. The cleaved products can be separated and concentrated from the intact peptide substrate by application of a directed electrophoretic field. Subsequent detection may be performed with a high sensitivity fluorescent, luminescent or electronic detection component device. The methods may employ a micro-titer plate, microarray, and microfocusing gel formats as research and diagnostic platform systems for a variety of applications.

II. Definitions

A "subject" refers to an animal. In some embodiments, the subject is a mammalian subject such as a human, non-human primate (e.g. rat, mouse or other rodent), or domesticated animal (e.g. dog, horse, cat, pig).

Generally, a "sample" represents a mixture containing or suspected of containing an analyte to be measured in an assay. Samples which can be typically used in the methods of the invention include bodily fluids such as blood, which can be anti-coagulated blood as is commonly found in collected blood specimens, plasma, urine, semen, saliva, cell cultures, tissue extracts and the like.

The term "specific binding" refers to binding between two molecules such as a ligand and a receptor and is characterized by the ability of a molecule (ligand) to associate with another specific molecule (receptor) in the presence of many other diverse molecules. Specific binding of a ligand to a receptor is also evidenced by reduced binding of a detectably labeled ligand to the receptor in the presence of excess of unlabeled ligand (i.e. a binding competition assay).

The term "antibody" (Ab) refers to a polypeptide with a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Immunoglobulin light chains are classified as either kappa or lambda, whereas immunoglobulin heavy chains are classified as gamma, mu, alpha, delta, or epsilon. The immunoglobulin heavy chains define the immunoglobulin classes (isotypes), IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An example of an immunoglobulin (antibody) structural unit includes a tetramer. Each tetramer is composed of two identical pairs of polypeptide chains, each pair having one "light" (about 25 kD) and one "heavy" chain (about 50-70 kD). Disulfide bonds connect the heavy chain and the light chain of each individual pair. Further, the two heavy chains of each binding pair are connected through a disulfide bond in the hinge region. Each heavy and light chain has two regions, a constant region and a variable region. The constant region of the heavy chain is identical in all antibodies of the same isotype, but differs in antibodies of different isotypes. The variable region located at the N-terminus of the heavy and the light chain includes about 100 to 110 or more amino acids and is primarily responsible for antigen recognition. The terms variable light chain ($V_L$) and variable heavy chain ($V_H$) refer to these light and heavy chains, respectively.

Antibodies exist, for example as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab, which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into a Fab monomer. The Fab monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

"Polypeptide" refers to a polymer in which the monomers are amino acids and are joined together through amide bonds, alternatively referred to as a peptide. When the amino acids are α-amino acids, either the l-optical isomer or the d-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the d- or l-isomer. The l-isomers are generally preferred. In addition, other peptidomimetics are also useful in the present invention. For a general review, see, Spatola, A. F., in Chemistry and Biochemistry of Amino Acids, Peptides and Proteins, B. Weinstein, eds., Marcel Dekker, New York, p. 267 (1983).

The phrase "amino acid" as used herein refers to any of the twenty naturally occurring amino acids as well as any modified amino acids. Modifications can include natural processes such as posttranslational processing, or chemical modifications which are known in the art. Modifications include, but are not limited to, phosphorylation, ubiquitination, acetylation, amidation, glycosylation, covalent attachment of flavin, ADP-ribosylation, cross linking, iodination, methylation, and the like.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides.

A "nucleoside analog" as used herein is defined in more detail below and includes analogs of ribonucleosides and deoxyribonucleosides and the triphosphates thereof. As described above, they are naturally occurring or non-naturally occurring, and derived from natural sources or synthesized. These monomeric units are nucleoside analogs (or "nucleotide" analogs if the monomer is considered with reference to phosphorylation). For instance, structural groups are optionally added to the sugar or base of a nucleoside for incorporation into an oligonucleotide, such as a methyl or allyl group at the 2'-O position on the sugar, or a fluoro group which substitutes for the 2'-O group, or a bromo group on the nucleoside base. The phosphodiester linkage, or "sugar-phosphate backbone" of the oligonucleotide analog is substituted or modified, for instance with methyl phosphonates, phosphorothioates, dithiophosphates, boranophosphates, or O-methyl phosphates.

The terms "NCDPS", "NCDAS", "NCDLS", "NCDNS" and "NCDPKS" stand for net charge differentiating protease substrate, net charge differentiating amylase substrate, net charge differentiating lipase substrate, net charge differentiating nuclease substrate and net charge differentiating protein kinase substrate, respectively. NCDPS, NCDAS, NCDLS, NCDNS and NCDPKS are characterized by a specific net charge. For instance, for NCDPS the net charge can be either neutral, negative (e.g. −1) or positive (e.g. +1). The net charge confers a particular migratory potential to the NCDPS upon exposure to an electric field. Therefore, NCDPS with a negative net charge will migrate towards the anode, whereas NCDPS with a positive net charge will migrate towards the cathode of an electrochemical device. However, neutral NCDPS exhibit no substantial migration potential in an electrical field. Examples for other charge differentiating enzyme substrates as disclosed herein are kinase substrates, methylransferase substrates and aminotransferase substrates. In general any substrate specific for an enzyme present in a bodily fluid sample can be used in the present methods and devices.

The term "non-amino acid groups" includes any biological molecule other than an amino acid. Examples for non-amino acid groups are monomers, polymers, oligomers, small molecules, hyaluronic acid, RNA/DNA fragments, glucosaminoglycan, polyethylene glycols, polyacrylamides, succinic acid, aminobutyric acid.

The term "isomeric amino acid" includes amino acids that are present in an optical isomeric form other than the L form. Examples are D-amino acids which are naturally found in proteins by exotic sea dwelling organisms, and are abundant components of the peptidoglycan cell walls of bacteria.

The term "reactive functional group" as used herein includes, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the crosslinking reactions disclosed herein. Alternatively, a reactive functional group can be protected from participating in the crosslinking reaction by the presence of a protecting group. Those of skill in the art will understand how to protect a particular functional group from interfering with a chosen set of reaction conditions. For examples of useful protecting groups, See Greene et al., Protective Groups in Organic Synthesis, John Wiley & Sons, New York, 1991.

III. Methods of Detecting Degradative Enzymes

In one aspect, a method of detecting a degradative enzyme in a bodily fluid sample is provided. The method includes the step of contacting the bodily fluid sample with a negatively charged degradative enzyme substrate or neutral degradative enzyme substrate. The degradative enzyme is allowed to react with the negatively charged degradative enzyme substrate or neutral degradative enzyme substrate thereby forming a positively charged degradative enzyme product. The positively charged degradative enzyme product is electrophoretically separated from the negatively charged degradative enzyme substrate or neutral degradative enzyme substrate. The separated positively charged degradative enzyme product is detected thereby detecting the degradative enzyme in the bodily fluid sample.

Within the bodily fluid sample is the degradative enzyme. Therefore, by contacting the bodily fluid sample with a negatively charged degradative enzyme substrate or neutral degradative enzyme substrate, the degradative enzyme (within the bodily fluid sample) is contacted with a negatively charged degradative enzyme substrate or neutral degradative enzyme substrate. Thus, in some embodiments, the degradative enzyme within the bodily fluid sample is contacted with the bodily fluid sample with a negatively charged degradative enzyme substrate or neutral degradative enzyme substrate.

A degradative enzyme is an enzyme with the ability to degrade (e.g. hydrolyze) biological molecules. In some embodiments, the degradative enzyme is a protease, a lipase, an amylase, or a nuclease. A protease is a degradative enzyme that cleaves peptide bonds linking amino acids in a polypeptide chain. A lipase is a degradative enzyme that cleaves ester bonds in lipid substrates. An amylase is a degradative enzyme that cleaves glycosidic bonds in polysaccharides. A nuclease is degradative enzyme that cleaves phosphodiester bonds in nucleic acids. In some embodiments, the degradative enzyme is a protease, such as a serine protease, a threonine protease, a cysteine protease, an aspartic acid protease, a metalloprotease or a glutamic acid protease. Degradative enzymes also include, but are not limited to chymotrypsin, trypsin, matrix metalloproteases, and thrombin. In some embodiments, the degradative enzyme is α-chymotrypsin, trypsin, elastase, matrix metalloproteinase-2 (MMP-2), MMP-9, MMP-14, or both α-chymotrypsin and trypsin.

Very low levels of degradative enzymes (e.g. chymotrypsin, trypsin, matrix metalloproteases, peptidases, thrombin, amylases, lipases, nucleases, kinases) may be detected directly in blood, plasma and other biological samples using the degradative enzyme substrates and other charge differentiating substrates provided herein. The degradative enzymes, in some embodiments, are the initiates and earlier indicators of shock, inflammation and many other disease processes.

A bodily fluid sample, as described herein, is a sample of fluid obtained from the body of a subject. Examples of a bodily fluid samples include, but are not limited to blood, plasma, serum, urine, saliva, synovial fluid, lymph fluid, semen, intestinal fluid samples, fecal fluid samples, milk, biopsy and smear samples and other biological or environmental samples. A bodily fluid sample, as disclosed herein, may include constituents that are detectable (e.g. fluorescent), charged and/or capable of migrating on a typical electrophoresis gel apparatus. In some embodiments, the detectable constituents of the bodily fluid sample are fluorescent.

In other embodiments, the bodily fluid sample is a crude bodily fluid sample. A "crude bodily fluid sample" refers to a bodily fluid sample containing the endogenous constituents of the bodily fluid sample as found in the subject and optionally additional assay components (e.g. buffers, stabilizing reagents, etc.). Thus, a crude bodily fluid sample is not the product of substantial purification or separation procedures, such as size exclusion filtering or separation centrifugation. In other embodiments, the bodily fluid sample is a crude blood sample or a crude lymphoid sample. In some embodiments, the bodily fluid sample is a crude blood sample.

In some embodiments, the bodily fluid sample is a semi-crude processed bodily fluid sample. A "semi-crude bodily fluid sample" is a bodily fluid sample containing at least 50% by weight of the endogenous constituents of the bodily fluid sample as found in the subject and optionally additional assay components.

In other embodiments, the bodily fluid sample is a processed interfering bodily fluid sample. A "processed interfering bodily fluid sample" is a bodily fluid sample which has been processed (e.g. partially purified, separated, concentrated etc.) but retains endogenous constituents of the bodily fluid sample as found in the subject.

In other embodiments, the bodily fluid sample is a cell-free bodily fluid sample. A "cell-free bodily fluid sample" is a bodily fluid sample from which all or some of the cellular constituents have been substantially removed. In some embodiments, the cell-free bodily fluid is blood plasma. In other embodiments, the bodily fluid sample is a processed cell-free bodily fluid sample. A "non-clotting blood sample" is a bodily fluid blood sample from which clotting factors have been substantially removed. In some embodiments, the non-clotting fluid sample is blood serum.

In some embodiments, the methods provided herein allow for rapid detection of degradative enzymes. The bodily fluid sample obtained from a subject may be used directly in the methods disclosed herein. In some cases, some minimal sample preparation may be employed such as adding agents to the sample, such as buffers, activating agents, stabilizing agents, and the like.

A degradative enzyme substrate is a molecule (e.g. a biological molecule) recognized and cleaved by a degradative enzyme. Upon cleavage, the degradative enzyme substrate is converted to a degradative enzyme product. Degradative enzyme substrates may include, but are not limited to, peptides, lipids, polysaccharides and nucleic acids. In some embodiments the degradative enzyme substrate is a negatively charged degradative enzyme substrate or a neutral degradative enzyme substrate. In some embodiments, the negatively charged degradative enzyme substrate or neutral degradative enzyme substrate includes a peptide, a lipid, a polysaccharide or a nucleic acid. In other embodiments, the negatively charged degradative enzyme substrate or neutral degradative enzyme substrate is a peptide.

The degradative enzyme substrates disclosed herein are typically designed to avoid unspecific cleavage by degradative enzymes present in the bodily fluid sample or other analysis constituents. To increase the specificity of degradative enzyme cleavage, an isomeric amino acid, a non-amino acid group, a stabilizing moiety or combinations thereof may be included in the degradative enzyme substrate at specific positions. In some embodiments, the isomeric amino acid is a D-amino acid. In other embodiments, the non-amino acid group is a polyethylene glycol. The position of the isomeric amino acid or non-amino acid group within the degradative enzyme substrate may be critical. In some embodiments, the isomeric amino acid or non-amino acid group is introduced near the cleavage recognition site. The cleavage recognition site is a specific sequence of biological molecules that is recognized and cleaved by a degradative enzyme. Upon introduction of the isomeric amino acid or non-amino acid group near the cleavage recognition site, cleavage by unspecific degradative enzymes is prevented. In some embodiments, the isomeric amino acid or non-amino acid group is positioned more than two to three residues from the cleavage recognition site of the degradative enzyme.

In some embodiments, the degradative enzyme substrate includes a stabilizing moiety. In order to prevent unspecific degradation of the degradative enzyme substrate, a stabilizing moiety may be included in the degradative enzyme substrate. Unspecific enzyme degradation may be caused by the presence of degradative enzymes such as peptidases or unspecific proteases present in the bodily fluid sample or the assay components. Examples of stabilizing moieties may include any appropriate chemical modification of an amino acid. Such chemical modifications may include for example phosphorylation, ubiquitination, acetylation, amidation, glycosylation, covalent attachment of flavin, ADP-ribosylation, cross linking, iodination, methylation, and the like.

In other embodiments, the degradative enzyme substrate includes a detectable moiety. A detectable moiety is a moiety that confers detectability to the degradative enzyme substrate using known methods in the art. For example, the degradative enzyme substrate may include detectable moieties such as organic fluorophores, detectable moieties employed in fluorescent energy transfer (FRET) systems, quantum dots, fluorescent nanoparticles, dendrimeric nanoparticle labels, gold and other metallic nanoparticles, carbon nanotubes, chemiluminescent labels, HRP, microperoxidase, alkaline phosphatase and electrochemical and oxidation/reduction labels for direct electronic detection. Examples for fluorophores include, but are not limited to, fluorescein isothiocyanate, rhodamine, coumarin, cyanine, Alexa Fluors, DyLight Fluors, luciferin, green fluorescent protein, fluorescein, Texas Red, Cy3, Cy5 and Bodipy dyes. Many such labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it is not readily available commercially, will be able to synthesize the necessary fluorophore de novo or synthetically modify commercially available fluorescent compounds to arrive at the desired fluorescent label. In some embodiments, the detectable moiety includes a positively charged fluorophore. In certain embodiments, the detectable moiety is a chemiluminescent moiety. In other embodiments, the detectable moiety is a fluorophore, a quantum dot, a fluorescent nanoparticle, a dendrimeric nanoparticle, a metallic particle, a chemiluminescent label, an electrochemical label or a oxidation/reduction label. In other embodiments, the detectable moiety is a fluorophore. In addition to conferring detectability, the detectable moiety may also change the net charge of the degradative enzyme substrate and the overall secondary specificity of the substrate for a specific enzyme. More, specifically, the fluorophore may be carefully considered as a modifying R-group for improving secondary specificity of the substrate.

The degradative enzyme substrate may include a detectable moiety or a stabilizing moiety. In some embodiments, the degradative enzyme substrate includes a detectable moiety and a stabilizing moiety. In some embodiments, the stabilizing moiety is attached to one end of the degradative enzyme substrate and the detectable moiety is attached to the opposite end of the degradative enzyme substrate. In some embodiments, where the degradative enzyme substrate is a peptide, the stabilizing moiety is attached to the N-terminal end of the degradative enzyme substrate and the detectable moiety is attached to the C-terminal end. In other embodiments, where the degradative enzyme substrate is a peptide, the detectable moiety is attached to the N-terminal end of the degradative enzyme substrate. In some embodiments, where the degradative enzyme substrate is a peptide, the stabilizing moiety is attached to the C-terminal end of the degradative enzyme substrate.

The detectable moiety may be covalently attached to the degradative enzyme substrate using a reactive functional group, which can be located at any appropriate position. When the reactive group is attached to an alkyl, or substituted alkyl chain tethered to an aryl nucleus, the reactive group may be located at a terminal position of an alkyl chain. Reactive groups and classes of reactions useful in practicing the present invention are generally those that are well known in the art of bioconjugate chemistry. Currently favored classes of reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Linkers may also be employed to attach the detectable moiety to the degradative enzyme substrate. Linkers may include reactive groups at the point of attachment to the detectable label and/or the mobile detectable analyte binding reagents. Any appropriate linker may be used in the present invention, including substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene. Other useful linkers include those having a polyester backbone (e.g. polyethylene glycol), nucleic acid backbones, amino acid backbones, and derivatives thereof. A wide variety of useful linkers are commercially available (e.g. polyethylene glycol based linkers such as those available from Nektar, Inc. of Huntsville, Ala.). The detectable moiety may also be non-covalently attached to the degradative enzyme substrate using any appropriate binding pair (e.g. biotin-streptavidin, his tags, and the like).

Upon degradative enzyme cleavage the degradative enzyme substrate is converted into a degradative enzyme product having a different net charge than the degradative enzyme substrate. The generation of a degradative enzyme product having a different net charge than the degradative enzyme substrate ensures efficient subsequent separation of the degradative enzyme product from the degradative enzyme substrate. Further, a positively charged degradative enzyme product can be separated from detectable constituents of the bodily fluid sample thereby increasing the detection sensitivity. In some embodiments, a degradative enzyme reacts with a negatively charged degradative enzyme substrate or neutral degradative enzyme substrate thereby forming a positively charged degradative enzyme product. In other embodiments, the positively charged degradative enzyme product is separated from detectable constituents of the bodily fluid sample.

As described above, the degradative enzyme substrate may include a detectable moiety. Upon reaction with the degradative enzyme, the detectable moiety becomes part of the positively charged degradative enzyme product and confers all the properties previously described for a detectable moiety to the positively charged degradative enzyme product. With the inclusion of a detectable moiety, the positively charged degradative enzyme product becomes detectable and thereby the degradative enzyme in the bodily fluid sample may be detected. In some embodiments, the negatively charged degradative enzyme substrate or neutral degradative enzyme substrate and the positively charged degradative enzyme product include a detectable moiety.

In some embodiments, the degradative enzyme substrate is attached to a solid support. Attachment of the degradative enzyme substrate is performed such that upon cleavage of the degradative enzyme substrate by the degradative enzyme the degradative enzyme product remains attached to the solid support. Attaching the degradative enzyme product to a solid support allows separation of the degradative enzyme product from the bodily fluid sample and other constituents after cleavage with the degradative enzyme. The choice of solid support for use in the present methods is based upon the desired assay format and performance characteristics. Acceptable solid supports for use in the present methods can vary widely. A solid support can be porous or nonporous. It can be continuous or non-continuous, and flexible or nonflexible. A solid support can be made of a variety of materials including ceramic, glass, silicon, metal, organic polymeric materials, or combinations thereof.

In order to detect a degradative enzyme in a bodily fluid sample the negatively charged degradative enzyme substrate or neutral degradative enzyme substrate is contacted, and in some cases incubated, with the bodily fluid sample for sufficient time to allow degradation of the substrate. In some embodiments, about 100 to about 1000 µl of the crude bodily fluid sample are contacted with the negatively charged degradative enzyme substrate or neutral degradative enzyme substrate. In other embodiments, about 1 to about 1000 µl of the crude bodily fluid sample are contacted with the negatively charged degradative enzyme substrate or neutral degradative enzyme substrate. In another embodiment, about 0.1 to about 10 µl of the crude bodily fluid sample are contacted with the negatively charged degradative enzyme substrate or neutral degradative enzyme substrate.

Another component of the method is the separation of the degradative enzyme product from the degradative enzyme substrate and detectable constituents of the bodily fluid sample prior to detection. This separation can be achieved through application of an electric field in combination with size exclusion. A specific net charge typically confers a differential migratory potential to the degradative enzyme product and the degradative enzyme substrate when an electric field strength is applied. Additionally, due to the difference in size between the degradative enzyme substrate and the degradative enzyme product, separation is also accomplished through size exclusion. In some embodiments, the positively charged degradative enzyme product is electrophoretically separated from the negatively charged degradative enzyme substrate or neutral degradative enzyme substrate. In some embodiments, the process of electrophoretically separating is performed using a gel electrophoresis. In another embodiment, the gel electrophoresis is a gradient gel electrophoresis.

The concept of the present invention can easily be applied to new diagnostic, monitoring and detection devices and systems which include, but are not limited to microtiter plate formats, focusing microgels (smart gels), lab-on-a-chip devices, micro/nanoarrays, microsensor devices and point of care (POC) systems which will utilize the unique net charge differentiating protease substrates (NCDPS). The methods provided herein may be designed to detect a variety of clinically important protease activities (and other markers) simultaneously in a multiplex format that include but are not limited to micro/nanoarrays, point of care systems and devices for critical care and emergency room applications.

In some embodiments, the devices and other charge changing substrate constructs (antibodies, etc.) are designed to detect the actual cleavage products, e.g., amino acid sequences that are derived from important elements of membrane receptors for physiological function (e.g. the extracellular domain of the insulin receptor, membrane adhesion receptor, growth factor receptors, and many others membrane receptors), plasma proteins, or functional receptors in specific organs (nicotinic receptor in the brain, amyloid protein in Alzheimers disease, glutamate receptors, adrenergic receptors, cholinergic receptors, amino acid transporters, selectins, glycocalyx proteins, and many others). In certain embodiments, the combined properties of the unique substrates and devices allow the cleaved product fragments to be rapidly and clearly separated from the substrate, blood cells and background blood and plasma components which can greatly interfere and limit the detection of very low levels of disease specific enzymes. Such analytical, research and diagnostic devices/systems may include and/or incorporate without limitation, electrophoretic, dielectrophoretic, microfluiduic manipulation and/or differentiation components; on-chip optical/fluorescent excitation (semiconductor lasers) and detection (APDs, CCDs, etc.) components; micro/nanoscale electrodes for manipulation and/or electrochemical, impedance, potentiometric and amperometric detection; and nanopore materials and components for separation and selection.

Figure 4A:
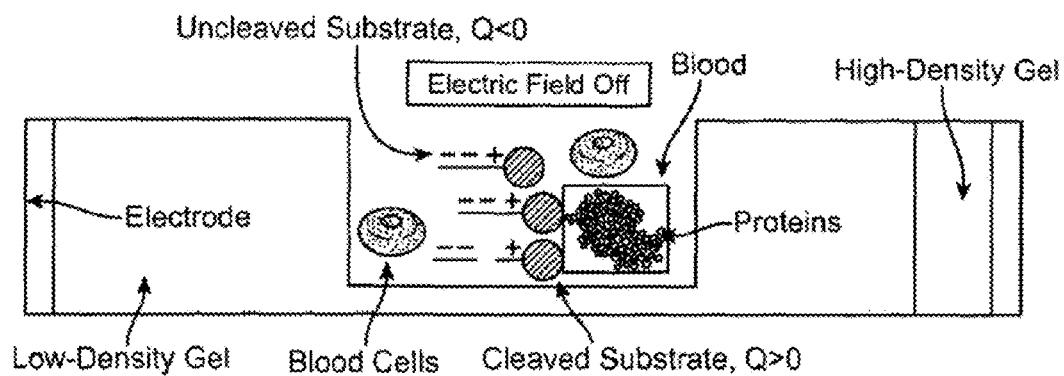
FIGS. 4A-4C. Cleavage and separation of the NCDPS substrate and product fragments in whole blood.
Figure 4B:
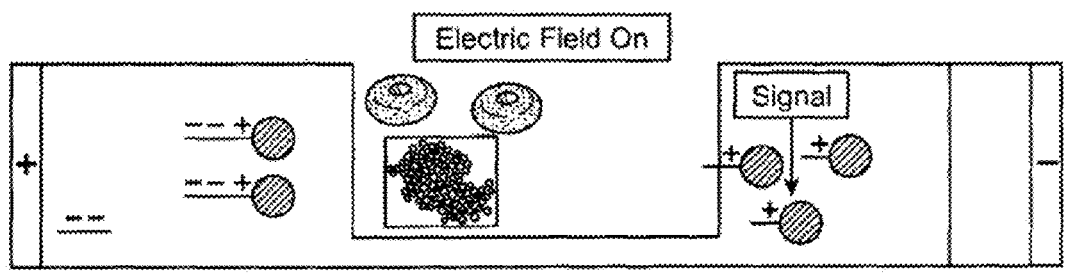
Figure 4C:
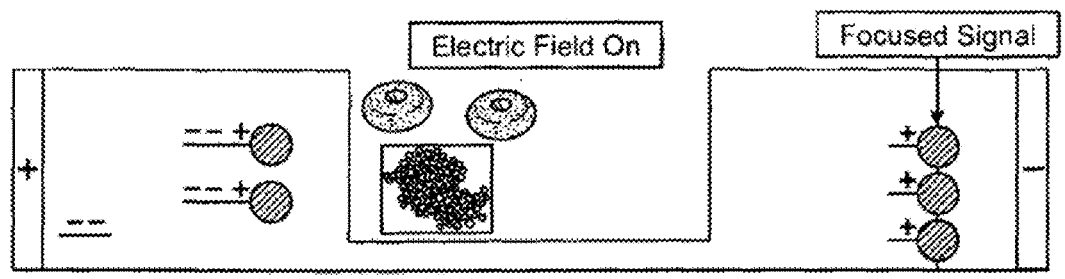

FIGS. 4A-4C show the advantages achieved from the combined properties of a unique substrate and device disclosed herein that allows cleaved product fragments to be rapidly and clearly separated from the original substrate, blood cells and background blood and plasma components. FIG. 4A first shows the negatively charged substrate mixed with blood within the sample well of the electrophoretic separation device, after being given a short time to react with a target enzyme (usually about one to thirty minutes). Cleavage of the substrate by the specific enzyme produces a positively charged fluorescent product fragment. In FIG. 4B the result of DC electric field application are shown. The positively charged fluorescent peptide cleavage fragment moves out from the sample well into a low density gel towards the negative electrode (anode) and is rapidly separated from blood cells which remain in the sample well. The un-cleaved negatively charged substrate and other blood and plasma components (mostly negatively charged proteins, hemoglobin, albumin etc.) migrate into the low density gel towards the positive electrode (cathode). The positively charged fluorescent peptide cleavage fragment moves quickly for a short distance where it reaches a high-density focusing gel. This focusing gel concentrates the product fragment into sharp narrow fluorescent band providing a higher signal to noise ratio for greatly improved detection sensitivity. Depending on the device design and sample well/chamber dimensions, the fluorescent peptide product fragment may only have to migrate less than one centimeter in a large scale device; less than a millimeter in a miniaturized device; or less than 100 microns in a microscale device. The actual separation time required depending on sample size may be less than one minute. Depending on the research or diagnostic application, devices can be designed for sample volumes that range from several milliliters to less than a nanoliter.

A variety of unique devices and systems are disclosed which work synergistically with the NCDPS substrates and methods of this invention for the rapid and highly sensitive detection of clinically relevant proteases and enzymes directly in blood, plasma and other clinical or biological samples. Depending on the application, these devices include but are not limited to microtiter plate formats, focusing gel/smart gel and focusing microgels in various cartridge formats, microarray devices in cartridge type formats. The devices can be used in association with power supplies, a manual or fluidic system for sample application, a fluorescent or other detection system and a computer based data collection system. These devices (microtiter plate, focusing gel, etc.) can also part of fully integrated laboratory or clinical diagnostic system which contains automated sample handling and integrated fluidics, detection, power and data processing components. In most cases, the sample cartridge devices are designed to be relatively inexpensive and disposal. In other aspects of the invention, smaller more compact devices and systems can be designed which are commonly called point of care (POC) systems, fully integrated portable field systems and even more miniaturized lab-on-a-chip systems. In certain cases the devices and systems of this invention have major advantages over more classical systems in that they eliminate or greatly reduce the need for any sample preparation (true sample to answer systems).

Figure 13:
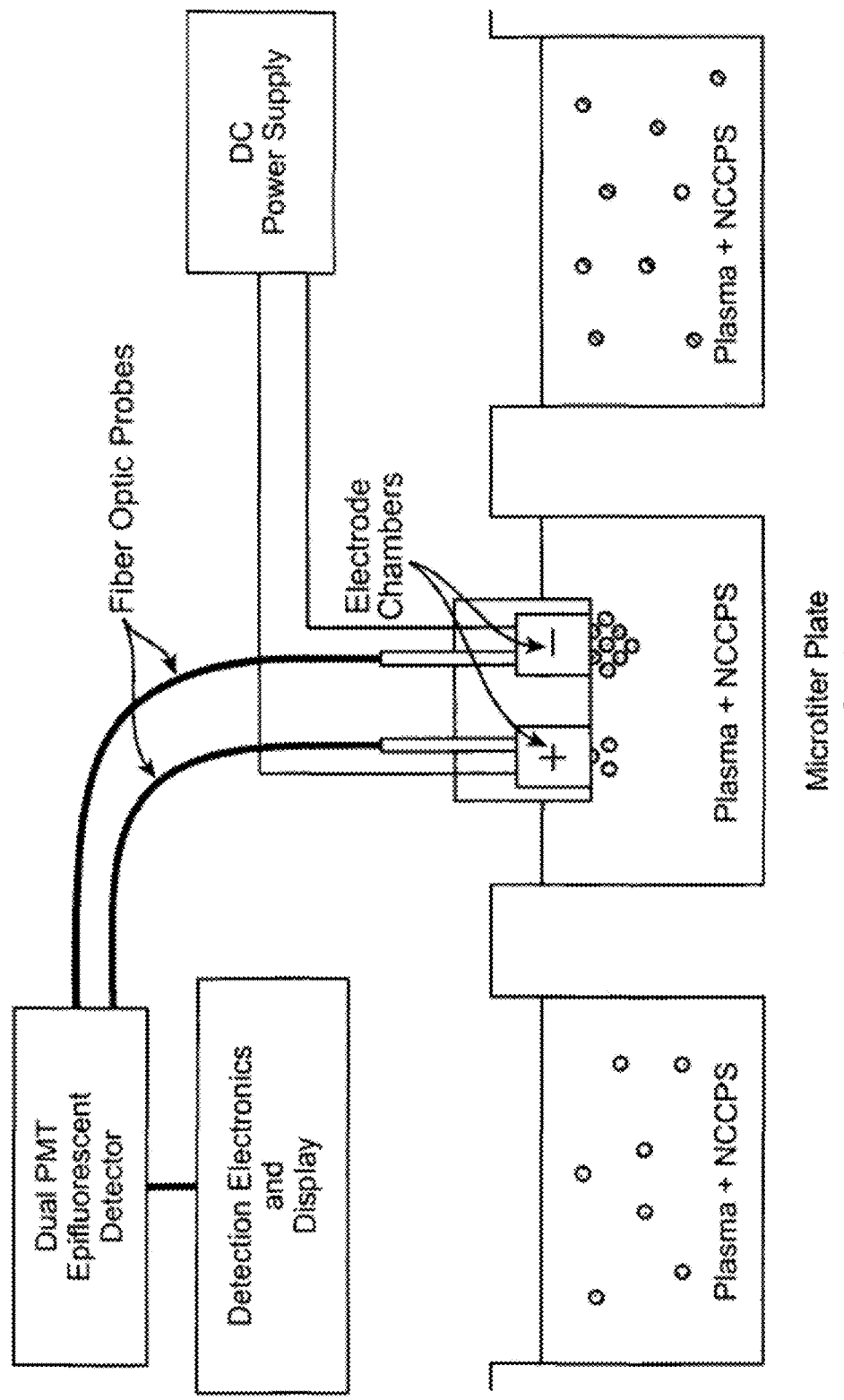
FIG. 13. Schematic of an enzyme separation and detection system in a microtiter plate format.

FIG. 13 shows the design for just one type of microtiter plate separation and detection system for multiple sample and/or multiplex degradative enzyme analyses using NCDPS substrates. In this case, blood or other samples mixed with the appropriate NCDPS (negatively charged substrates) are placed in the sample wells of the microtiter plate separation/detection device. After being given a short time to react with the target enzyme in the sample (generally one to thirty minutes), cleavage of the substrate by the target enzyme produces the positively charged fluorescent product fragments. When the DC electric field is applied, the positively charged degradative enzyme product moves through the sample chamber toward the negative electrode (anode). The positively charged degradative enzyme products are rapidly separated from blood cells, un-cleaved negatively charged substrate and other blood and plasma components (mostly negatively charged proteins, hemoglobin, albumin etc.) which migrate towards the positive electrode (cathode) on the opposite side of the microtiter plate sample chamber.

In the case of this format, the electrodes are placed behind a microtiter plate chamber wall which can be composed of a porous membrane (cellulose, nylon, plastic, etc.), a controlled pore filter material (glass, ceramic, etc) or an agarose/polyacrylamide gel composite which separates the electrodes from the actual sample chambers. The positively charged degradative enzyme product moves quickly for a short distance where it reaches the sample chamber wall. At this point, the microtiter plate walls can either be designed with a high pore density structure such that the fluorescent fragments concentrate onto the wall itself, or quickly migrate through the wall with low pore density structure and then concentrate or focus on a high pore density gel or other material for enhanced detection. In most cases, the entire separation and detection time after the sample reaction would be less than five minutes. Thus, the total sample to answer time for most applications could be less than thirty minutes. In most cases for this format, the focused fluorescent bands can be scanned and detected by an epifluorescent or other suitable fluorescence/luminescence detector device.

Another type of device which this invention discloses are focusing gel and smart gel formats which can be designed in large scale, miniature scale and microscale forms. These formats are somewhat akin to electrophoretic horizontal/submarine and vertical gel formats. Such focusing gel devices can also be designed in multiple tube and capillary formats. A focusing gel normally concentrates the fluorescent band in just the z-dimension (makes a broad fluorescent band much narrower). A smart gel is designed in a way that causes the fluorescent band to concentrate in all three dimensions (X-Y-Z). More specifically, a broad fluorescent band would now be focused or concentrated into a mall point of intense fluorescence. Smart gel formats involve the construction of cone shape structure through which the fluorescent band migrates.

Figure 14A:
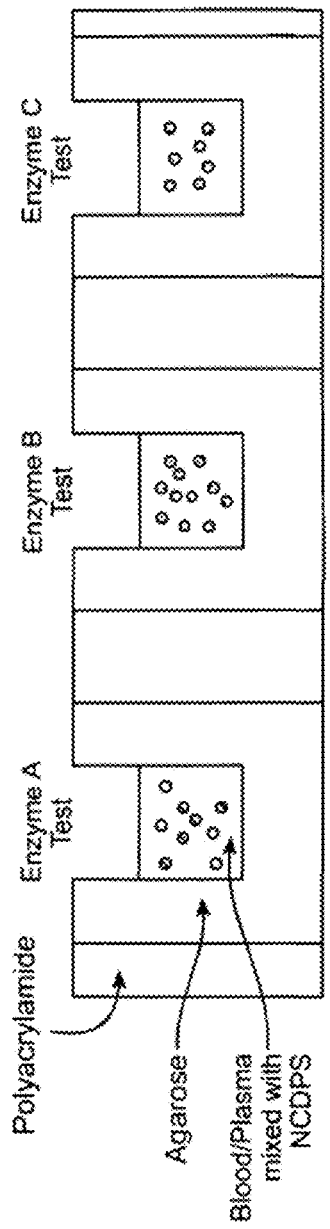
FIGS. 14A-14B. Schematic of an enzyme separation and detection system in a focusing/smart gel format.
Figure 14B:
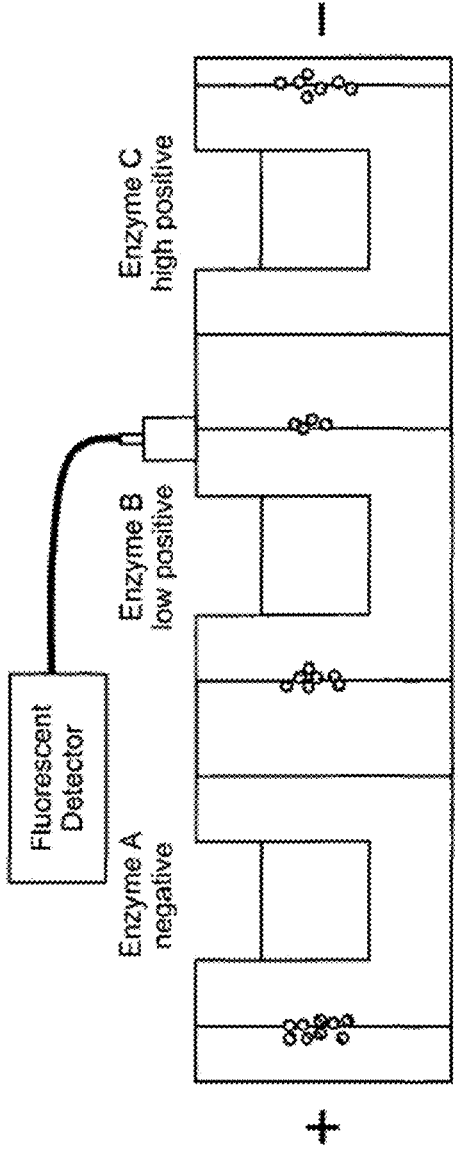

FIG. 14A shows the design for just one type of focusing gel system for multiple sample and/or multiplex enzyme analyses using NCDPS substrates. In this case, blood or other samples mixed with the appropriate NCDPS (negatively charged substrates) are placed in the sample wells of the device. After being given a short time to react with the target enzyme in the sample (generally one to thirty minutes), cleavage of the substrate by the target enzyme produces the positively charged fluorescent product fragments. When the DC electric field is applied, the positively charged degradative enzyme product moves from the sample chamber toward the negative electrode (anode). The positively charged degradative enzyme products are rapidly separated from blood cells, un-cleaved negatively charged substrate and other blood and plasma components (mostly negatively charged proteins, hemoglobin, albumin etc.) which migrate towards the positive electrode (cathode). The positively charged degradative enzyme product moves quickly for a short distance into the low pore density gel and then reaches a high pore density gel or other material which concentrates and focuses the fluorescent fragment for enhanced detection. In most cases, the entire separation and detection time after the sample reaction would be less than five minutes. Thus, the total sample to answer times for most applications could be less than thirty minutes. In most cases for these formats the focused fluorescent bands can be scanned and detected by an epifluorescent or other suitable fluorescence/luminescence detector device. In miniaturized or microscale versions of this device, detection would be carried out by an integrated detector system using wave guides, diode lasers and a solid state CMOS or avalanche photodiode detector.

In some embodiments, a non-fluorescent negatively charged polymeric entity (polyglutamic acid, DNA, etc.) can be run from the opposite direction of the focusing gel so that it meets the positively charged fluorescent fragment, which becomes neutralized, non-mobile and more highly focused. This technique further improves the gel focusing process and subsequent detection sensitivity. This same strategy can be used as a trigger mechanism for very sensitive chemiluminescent detection where a positively charged peptide fragment with a chemiluminescent label meets a chemiluminescent catalytic molecule such as peroxidase or a luciferase. Another similar strategy can be used where a positively charged peptide fragment with an oxidation or reduction label is moved from the reaction chamber through a gel into an electrochemical sensor or detecting element. For the various devices described above, particularly if designed to be disposable, sample chambers into which the reagents (substrates) have been pre-filled or lyophilized will have a significant advantage of producing a one step assay. A sample (blood, plasma, etc.) is added to the device and the assay is run without the need to add any reagents.

Figure 15:
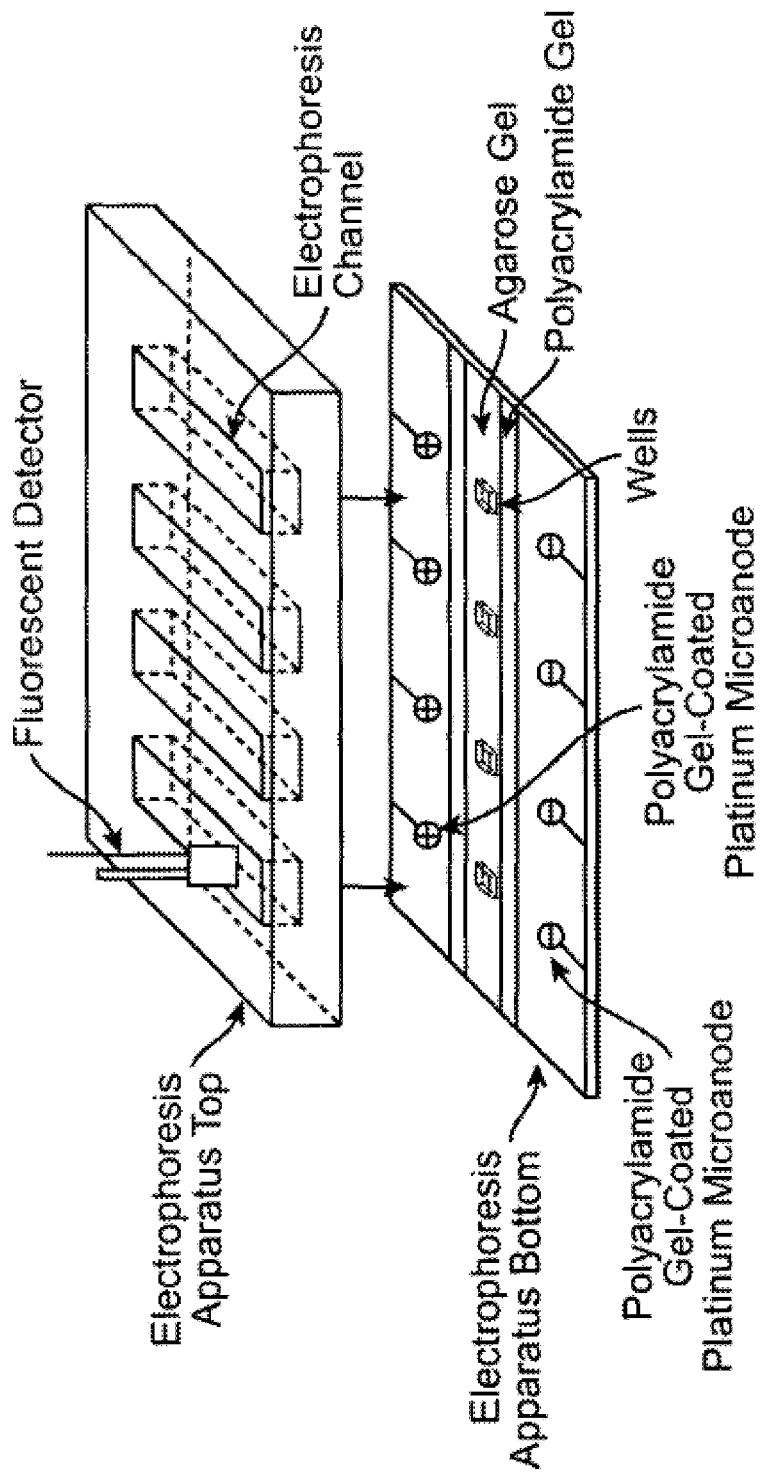
FIG. 15. Schematic of an enzyme separation and detection system in a microelectrode array format.
Figure 16:
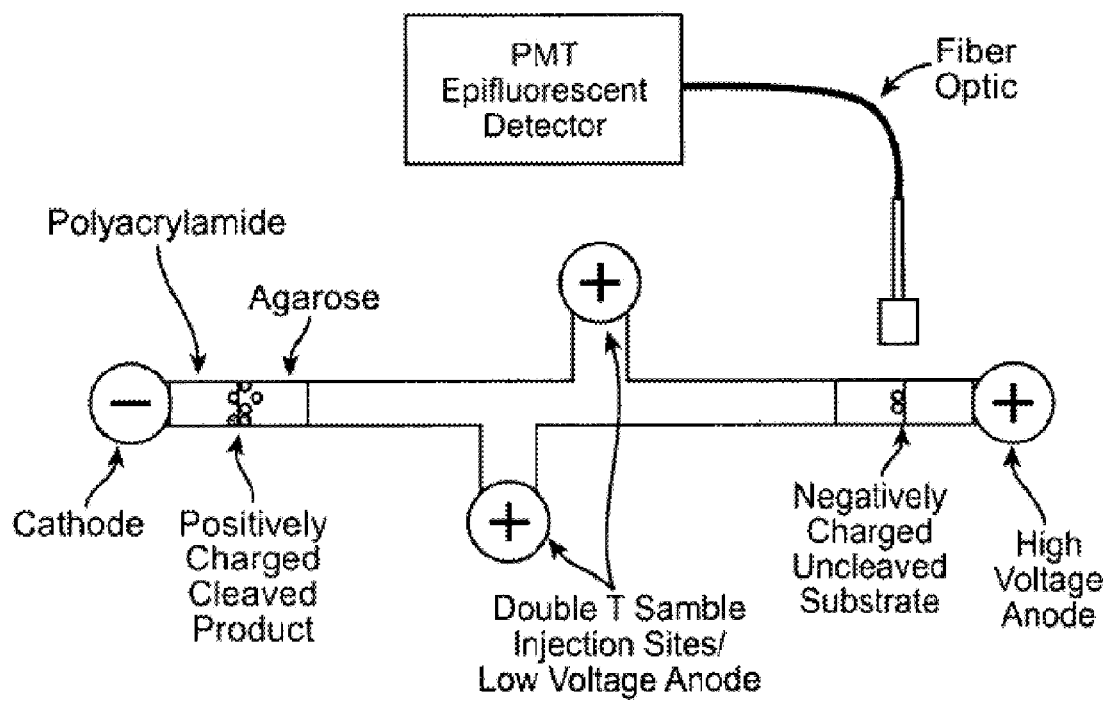
FIG. 16. Schematic of an enzyme separation and detection system in a microfluidic format.
Figure 17:
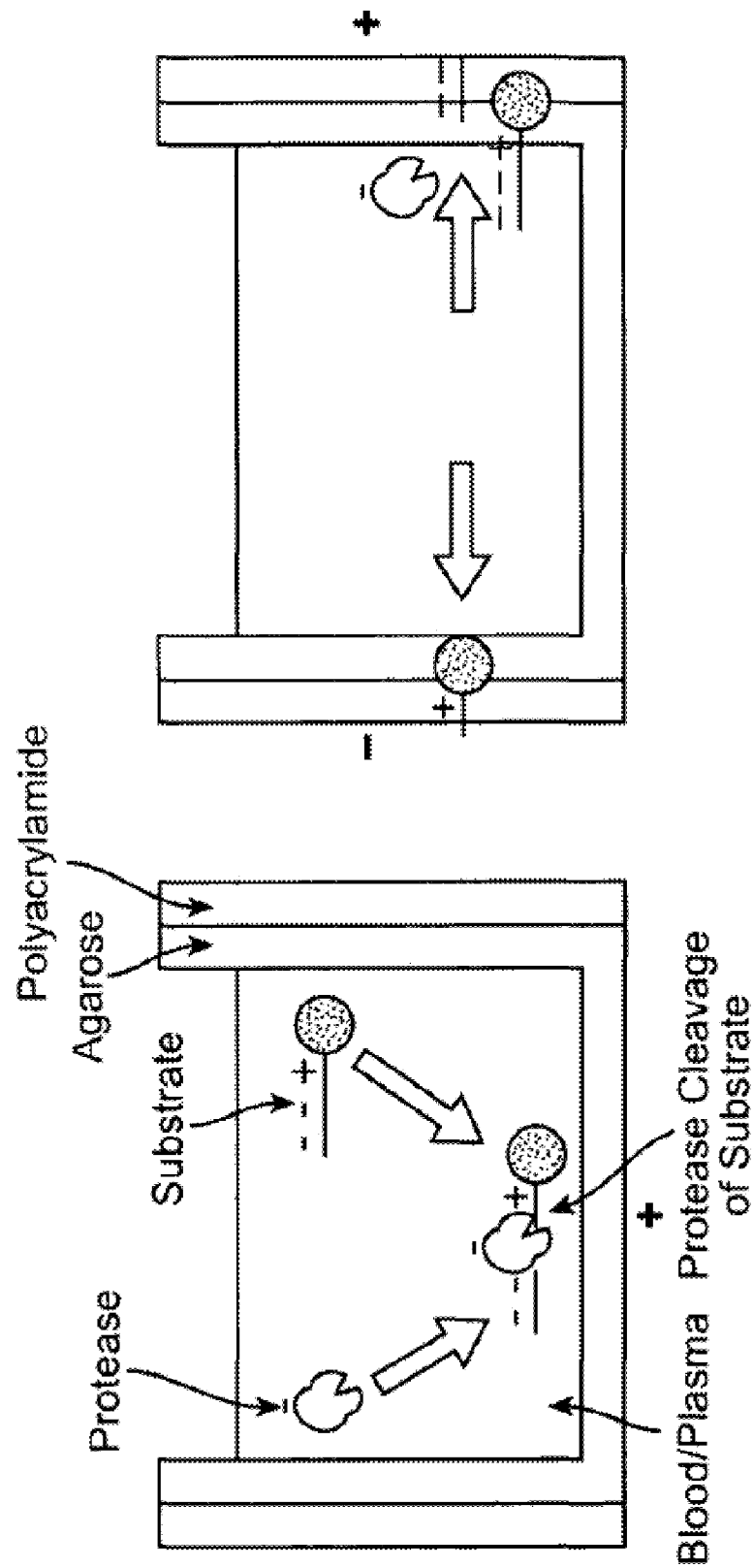
FIG. 17. Schematic of an enzyme separation and detection system which accelerates the reaction of the protease with the NCDPS substrates.
Figure 19:
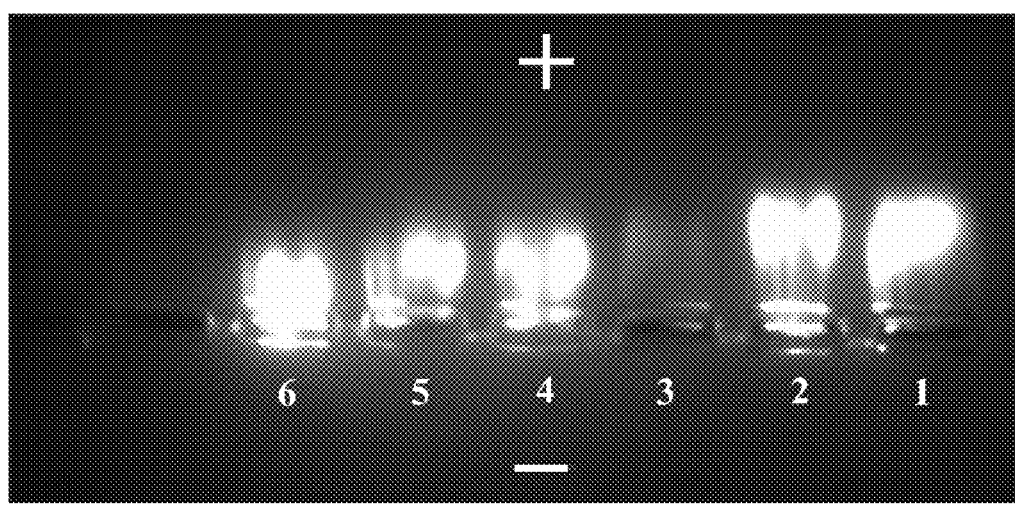
FIG. 19. Reduction of electrophoretic mobility of Streptavidin Quantum Dot-Biotinyl-Gln-His-Trp-Ser-Tyr-Gly-Leu-Arg-Pro-Gly-NH2 derivative (SEQ ID NO:24) (Example 1).

Other devices which represent just a few of the many possible devices of this invention are discussed below. FIG. 15 shows the concept for a microelectrode array type smart gel device. FIG. 16 shows the concept for a microfluidic type smart gel device. FIG. 17 shows the concept for a protease reaction accelerator and detector device.

In some embodiments, the total time to detect protease activity in the invention has two main considerations: (1) the time it takes for the reaction of the protease and net charge differentiating protease substrate and (2) the time it takes for electrophoresis of the fluorescent cleavage products and the subsequent detection of the fluorescence. The latter can be performed rapidly (seconds to minutes) because of the "Smart Gel" technology and because of highly sensitive fluorescent detectors (charge coupled device (CCD) cameras, photomultiplier tubes (PMT)). The former, therefore, can be the rate limiting step for this detection scheme if the reaction takes longer then the electrophoresis/detection time.

In order to reduce the reaction time, there are several options available: (1) introduce more substrate into the detection sample in order to improve reaction kinetics or (2) use an electric field to concentrate the degradative enzyme and the degradative enzyme substrate together to improve reaction kinetics. The latter method is cheaper as it does not require additional reagents, but instead concentrates the reagents already present in the detection sample. This works because the degradative enzyme and the degradative enzyme substrate are both negatively charged and can be actively concentrated with an electric field.

The device shown in FIG. 17 achieves this by first using an electric field to concentrate the negatively charged substrate and protease into one part of the device to accelerate the reaction kinetics, and then uses the electric field to concentrate the positively charged fluorescent product fragments into another part of the device for detection. FIG. 18 shows another version of this concept, but in this case the fluorescent substrate is immobilized to the surface of the device to where the protease will be concentrated. Such devices with immobilized substrates or with sample chambers where the reagents (substrates) have been lyophilized have a significant advantage in that samples can be applied and run without the need to add a reagent.

As described above methods are provided that, in some embodiments, rapidly separate a positively charged degradative enzyme from a negatively charged or neutral degradative enzyme substrate and constituents of the bodily fluid sample. In those embodiments where the degradative enzyme product includes a detectable moiety, the degradative enzyme product may be readily detected subsequent to the separation process. Detection units such as epifluorescent detectors, electrochemical detectors or chemiluminescent detectors may be used in the methods described herein. In some embodiments, detecting the separated positively charged degradative enzyme product includes detecting a fluorophore. In some embodiments, the fluorescent signal can be readily resolved from background components by two mechanisms: (a) exclusion of background components larger then fluorescent product fragment by filtration (e.g. in an electrophoretic gel, blood cells cannot leave the sample loading well because they are too large to migrate into the pores of the gel) and (b) exclusion of background components that are the same size as or smaller then the fluorescent product fragment because of opposite charge (e.g. in an electrophoretic gel, positively charged fluorescent product will migrate in the opposite direction from negatively charged proteins, blood cell fragments, etc.). In another embodiment, detecting the separated positively charged degradative enzyme product includes detecting a chemiluminescent label.

The specific features of the degradative enzyme substrates have been described herein. They may include a stabilizing moiety, a detectable moiety, a particular net charge and additional features conferring specificity for a particular degradative enzyme. The following table discloses certain useful specific peptide sequences. In some embodiments, the methods described herein include a negatively charged degradative enzyme substrate or neutral degradative enzyme substrate including one or more of the amino acid sequences (also referred to herein as peptide sequences) set forth as SEQ ID NOs:1-18 and conservative amino acid substitutions thereof.

In some embodiments, the negatively charged degradative enzyme substrate or neutral degradative enzyme substrate includes one or more of the amino acid sequence set forth as SEQ ID NOs:1-18 or conservative amino acid substitutions thereof and a detectable moiety. In another embodiment, the detectable moiety is a fluorophore, a quantum dot, a fluorescent nanoparticle, a dendrimeric nanoparticle, a metallic nanoparticle, a chemiluminescent label, a electrochemical label or a oxidation/reduction label. In another embodiment, the detectable moiety is a fluorophore. In one embodiment, the detectable moiety is a chemiluminescent label.

In other embodiments, the negatively charged degradative enzyme substrate or neutral degradative enzyme substrate includes one or more of the amino acid sequence set forth as SEQ ID NOs:1-7 or conservative amino acid substitutions thereof and a stabilizing moiety (as described above). In other embodiments, the negatively charged degradative enzyme substrate or neutral degradative enzyme substrate includes one or more of the amino acid sequence set forth as SEQ ID NOs:1-7 or conservative amino acid substitutions thereof, a detectable moiety, and a stabilizing moiety.

TABLE 1

| SEQ ID NO: | NCDPS Amino Acid Sequence | Degradative Enzyme |
|---|---|---|
| 1 | Gly-Asp-Ala-Gly-Tyr-/-Ala-Gly-Ala-Gly-Lys | α-Chymotrypsin |
| 2 | Asp-Gly-Asp-Ala-Gly-Arg-/-Ala-Gly-Ala-Gly-Lys | Trypsin |
| 3 | Asp-Ala-Gly-Ser-Val-Ala-Gly-Ala-Gly-Lys | Elastase |
| 4 | Gly-Asp-(Leu-Ala-Ala-/-Ile-Thr-Ala)-Ala-Gly-Ala-Gly-Lys | MMP-2 |
| 5 | Gly-Asp-(Pro-Val-Gly-/-Leu-Thr)-Ala-Gly-Ala-Gly-Lys | MMP-9 |
| 6 | Gly-Asp-(Leu-Ile-Ser-His-Ser-/-Ile)-Ala-Gly-Ala-Gly-Lys | MMP-14 |
| 7 | Asp-Gly-Asp-Ala-Gly-Tyr-/-Ala-Gly-Leu-/-Arg-/-Gly-Ala-Lys | Chymotrypsin, Trypsin |
| 8 | Acetyl-N-Gly-Asp-Ala-Gly-Tyr-/-Ala-Gly-Ala-Gly-Lys(Bodipy TR)-NH2 | α-Chymotrypsin |
| 9 | Acetyl-N-Asp-Gly-Asp-Ala-Gly-Arg-/-Ala-Gly-Ala-Gly-Lys(Bodipy TR)-NH2 | Trypsin |
| 10 | Acetyl-N-Asp-Ala-Gly-Ser-Val-Ala-Gly-Ala-Gly-Lys(Bodipy TR)-NH2 | Elastase |
| 11 | Acetyl-N-Gly-Asp-(Leu-Ala-Ala-/-Ile-Thr-Ala)-Ala-Gly-Ala-Gly-Lys(Bodipy TR)-NH2 | MMP-2 |
| 12 | Acetyl-N-Gly-Asp-(Pro-Val-Gly-/-Leu-Thr)-Ala-Gly-Ala-Gly-Lys(Bodipy TR)-NH2 | MMP-9 |
| 13 | Acetyl-N-Gly-Asp-(Leu-Ile-Ser-His-Ser-/-Ile)-Ala-Gly-Ala-Gly-Lys(Bodipy TR)-NH2 | MMP-14 |
| 14 | Acetyl-N-Asp-Gly-Asp-Ala-Gly-Tyr-/-Ala-Gly-Leu-/-Arg-/-Gly-Ala-Lys(Bodipy TR)-NH2 | Chymotrypsin, Trypsin |
| 15 | N-Ac-Asp-PEG-Gly-Tyr-/-Ala-Gly- PEG-Bodipy TR | Chymotrypsin |
| 16 | N-Ac-Asp-Asp-PEG-Gly- Arg-/-Ala-Gly-PEG-Bodipy TR | Trypsin |
| 17 | Acetyl-N-Gly-(D-Asp)-(D-Ala)--Gly-Tyr-/-Ala-Gly-(D-Ala)-Gly-(D-Lys)(Bodipy TR)-NH2 | Chymotrypsin |
| 18 | Acetyl-N-(D-Asp)-Gly-(D-Asp)-(D-Ala)-Gly-Arg-/-Ala-Gly-(D-Ala)-Gly-(D-Lys)(Bodipy TR)-NH2 | Trypsin |

The specific protease peptide substrates listed above represent just a few of the potential sequences which can be designed and synthesized. The sequences shown above are labeled via the ε-amino group of lysine with a Bodipy TR fluorophore, and the terminal α-amino groups are acetylated and the terminal α-carboxyl groups are modified to form an amide group (thus the terminal ends of these particular peptide substrates are not charged). It should be pointed out that other design parameters which include end labeling with an appropriate fluorescent groups, and maintaining charge on the terminal ε-amino group and/or the terminal α-carboxyl group can be used when they produce the separation and detection advantages discussed in this invention. For the above sequences the basic design parameters include specific amino acid cleavage sequences (for specific proteases), and appropriate chemistry for further derivatization with an appropriate fluorescent label. A wide variety of modification and derivatization chemistries are well known in the art for attaching fluorescent and other detection moieties to peptides. But included herein are also other novel design parameters which reduce secondary cleavage by other proteases (which might be found normally in blood) and most importantly, produce a positively charged cleavage fragment from a negatively charged or neutral substrate when cleaved by the specific protease.

Other types of novel Net Charge Differentiating Protease Substrates (NCDPS) that include a short (2-6 residue) amino acid recognition/cleavage site surrounded by either D-amino acids or non-amino acid groups (either on one side or both sides and that can be charged or uncharged) are hereby disclosed. Previously known peptide substrates (often fluorogenic or chromogenic) typically have limited specificity for their intended protease targets since they ignore a protease's specificity on the c-terminal side of the scissile (cleavage) bond. Longer peptide substrates (e.g. NCDPS, fluorescent resonant energy transfer substrates) can be made to create more specific substrates that account for this missing sub-site specificity. They also may allow for conjugation of various types of fluorescent moieties at greater distances from the scissile bond in order to reduce steric hindrance from the fluorophore, which would reduce the substrate's ability to enter the protease's active site.

The introduction of D-amino acid and non-amino acid groups may also help to limit the introduction secondary cleavage sites into the substrate. Additionally, it allows for the incorporation of other properties into these substrates, such as special arrangements of the charged groups to eliminate non-specific binding, better solubility properties or selective steric hindrance which would allow substrate to be more efficiently cleaved by its specific protease, but not by a closely related protease which has some specificity for the same cleavage site. However, as these substrates become longer, there is a risk of increasing the amount of non-specific proteolytic cleavage. As the number of L-amino acids in the substrate increases, there are potentially more cleavage sites for proteases that were not intended to cleave that substrate. Thus, in order to obtain a substrate long enough to a) allow for optimal spacing between the scissile bond and the fluorophore, b) include desired charge and solubility properties, and c) and include c-terminal sub-site specificity without increasing non-specific cleavage, new substrates can be made that incorporate D-amino acids and non-amino acid groups into the substrate. They will provide the desired properties of the substrate while allowing the specificity of the substrate to be maintained or improved. The use of D-amino acids represents just one example of designing more specific NCDPS substrates For example, Acetyl-N-Gly-Asp-Ala-Gly-Tyr–/–Ala-Gly-Ala-Gly-Lys(Bodipy TR)-NH$_2$ (SEQ ID NO:8) and Acetyl-N-Asp-Gly-Asp-Ala-Gly-Arg–/–Ala-Gly-Ala-Gly-Lys(Bodipy TR)—NH$_2$ (SEQ ID NO:9) are a chymotrypsin and trypsin NCDPS, respectively. They are cleaved on the C-terminal side of the tyrosine and arginine residues, respectively. Many of the residues in those substrates may serve primarily to introduce sufficient space between the scissile bond and the fluorescent moiety and to give the substrate the desired charge changing properties when it is cleaved. It is possible that non-specific proteases such as elastase and proteinase K can still cleave this substrate (albeit with relatively low activities compared to chymotrypsin and trypsin). Examples of substrates that take advantage of non-amino acids would be the following:

```
Chymotrypsin Substrate:
                                        (SEQ ID NO: 26)
N-Ac-Asp-PEG-Gly-Tyr-/-Ala-Gly- PEG-Bodipy TR Trypsin Substrate:
                                        (SEQ ID NO: 27)
N-Ac-Asp-Asp-PEG-Gly- Arg-/-Ala-Gly- PEG-Bodipy TR
```

Note: PEG=Polyethylene Glycol, and "–/–" denotes the scissile bond
Similarly, additional substrates can be obtained by incorporating D-amino acids as follows:

```
Chymotrypsin Substrate:
Acetyl-N-Gly-(D-Asp)-(D-Ala)--Gly-Tyr-/-Ala-Gly-(D-Ala)-Gly-
(D-Lys)(Bodipy TR)-NH2

Trypsin Substrate:
Acetyl-N-(D-Asp)-Gly-(D-Asp)-(D-Ala)-Gly-Arg-/-Ala-Gly-(D-Ala)-Gly-
(D-Lys)(Bodipy TR)-NH2
```

Note: Bodipy TR is conjugated to the epsilon-amino of the Lysine and these peptides' c-termini are amidated.

In addition to substrates with small organic fluorophore, luminescent molecule (luminol, etc.) and oxidation/reduction molecule labels, the methods include the use of larger fluorescent, luminescent, and chemiluminescent macromolecules and nano-entities, which can include but are not limited to fluorescent nanoparticles, quantum dots, metallic nanoparticles and nanorods (gold, silver, platinum, semiconductor materials, etc), dendrimers, fluorescent proteins (phycobiliproteins, fluorescent antibodies, fluorescent streptavidin, etc), bioluminescent proteins (peroxidase, alkaline phosphatase, luciferase, calmodulin, etc.) and oxidation/reduction proteins and nanoparticles.

Figure 7:
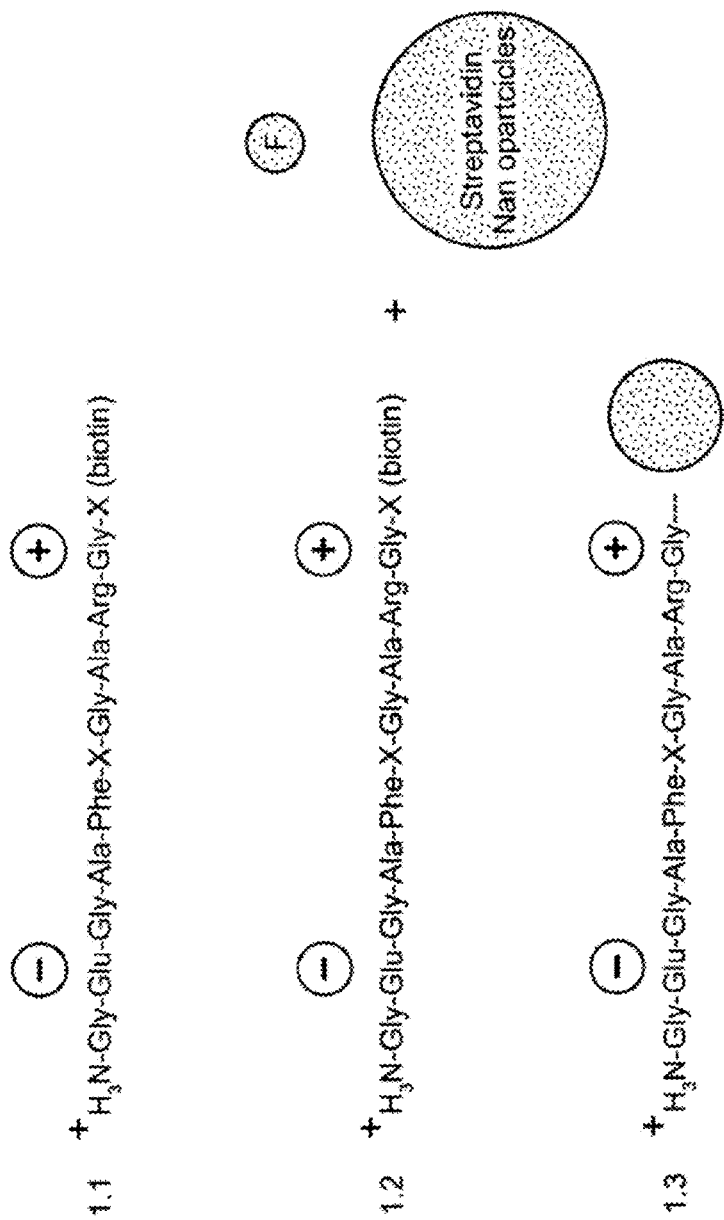
FIG. 7. Design and synthesis of the net charge differentiating peptide substrate (NCDPS) with a streptavidin Quantum Dot or fluorescent nanoparticle label. Sequence: Gly-Glu-Gly-Ala-Phe-Gly-Ala-Arg-Gly-(biotin) (SEQ ID NO:23); Gly-Glu-Gly-Ala-Phe-Gly-Ala-Arg-Gly (SEQ ID NO:22).

FIG. 7 shows a scheme for the design of an NCDPS chymotrypsin specific substrate with a fluorescent streptavidin nanoparticle label. This particular design allows a biotinylated peptide sequence to be attached to the nanoparticle via the biotin-streptavidin ligand binding. However, the peptide sequences can also be attached to the nanoparticles covalently. The fluorescent nanoparticle peptide substrate is designed such that it has net negative or neutral charge until a specific protease cleaves the peptide producing a fluorescent nanoparticle product with a net positive charge. In some embodiments, this invention relates to nanoparticles, macromolecules (proteins, dendrimers, etc.), modified polymers and biopolymers, as well as surface materials (glass, plastic, silicon, gold etc.) being used for the attachment of a degradative enzyme substrate molecule. In this case, a non-fluorescent nanoparticle (macromolecule, dendrimer, polymer, surface material) would be derivatized with a degradative enzyme substrate, which upon cleavage by a specific protease or other enzyme releases a fluorescent peptide fragment which then can be readily separated from the nanoparticles and other components of the sample.

Figure 8:
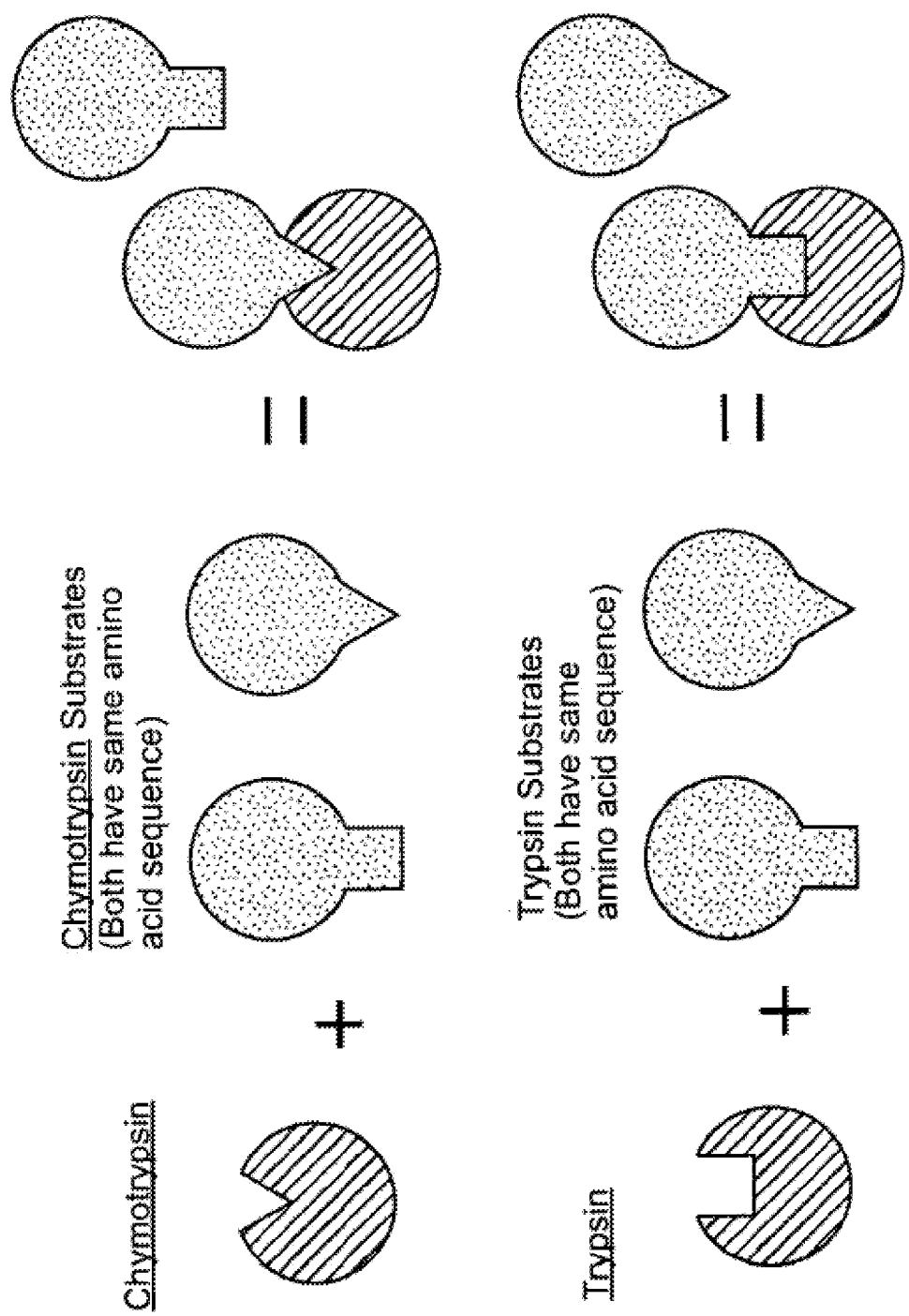
FIG. 8. 3D or tertiary NCDPS substrates. Two substrates are shown for chymotrypsin and trypsin that have the same amino acid sequence, but different tertiary structures.

Other novel more three dimensional Net Charge Differentiating Protease Substrates (NCDPS) with improved specificity due to more tertiary structure that better mimics the protease's natural biological substrates (a protein molecule) are hereby also disclosed in this invention. Such substrates can improve the ability to distinguish between similar proteases that recognize similar amino acid sequences, such as to distinguish matrix-metalloproteases (MMPs) of which there are 28 known so far, and to distinguish trypsin-like proteases (trypsin, kallikrein, plasmin, and thrombin) from each other. Biological substrates for proteases are generally 3-dimensional proteins which in addition to the specific amino acid cleavage sites have conformation around that sequence site to which a specific protease must be able to fit in order for the protease's active site to catalyze the cleavage of the specific sequence (see FIG. 8). More tertiary or three-dimensional structures can be mimicked in a number of ways, such as by incorporating prolines to introduce kinks in the peptide and by strategically introducing amino acids or other entities with bulkier side chains of various sizes. These modifications would be done to better aid a substrate to fit more specifically into the target protease's active site and less well into the active site of a closely related protease. Because the three dimensional structures around many of the true natural substrates are not known, these more three dimensional substrate structures would have to be initially determined by a combinatorial process, which might require the use of complex peptide arrays. However, this method includes the use of a small library of 10 to 12 peptide sequences in which one or two prolines and several bulkier D-amino acids or L-amino acids such as tryptophan, phenylalanine, isoleucine, glutamine, arginine are randomly arranged about three to six amino acid away from the cleavage site. The small libraries would thus test a variety of three dimensional projections around the basic cleavage site. The first small library of peptides would be tested against three or four closely related proteases (MMP's for example) to determine which has the most specificity. Once a unique peptide substrate is determined, a second library group of 10 to 12 peptides would be designed with further modification around the particular proline/bulky amino acid sequence which is imparting the higher specificity. A uniquely specific peptide substrate should be determined from this second library group of peptide substrates.

Figure 9:
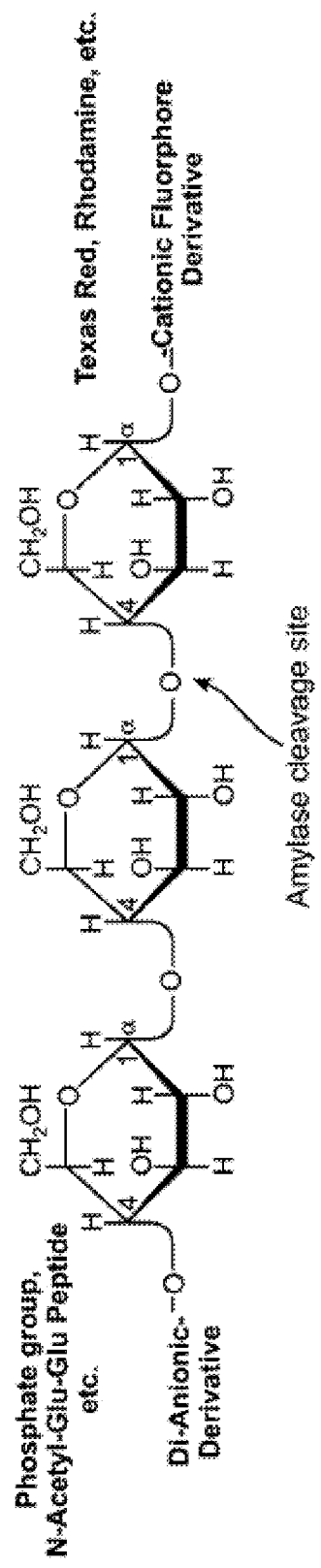
FIG. 9. Design for net charge changing amylase substrate.
Figure 10:
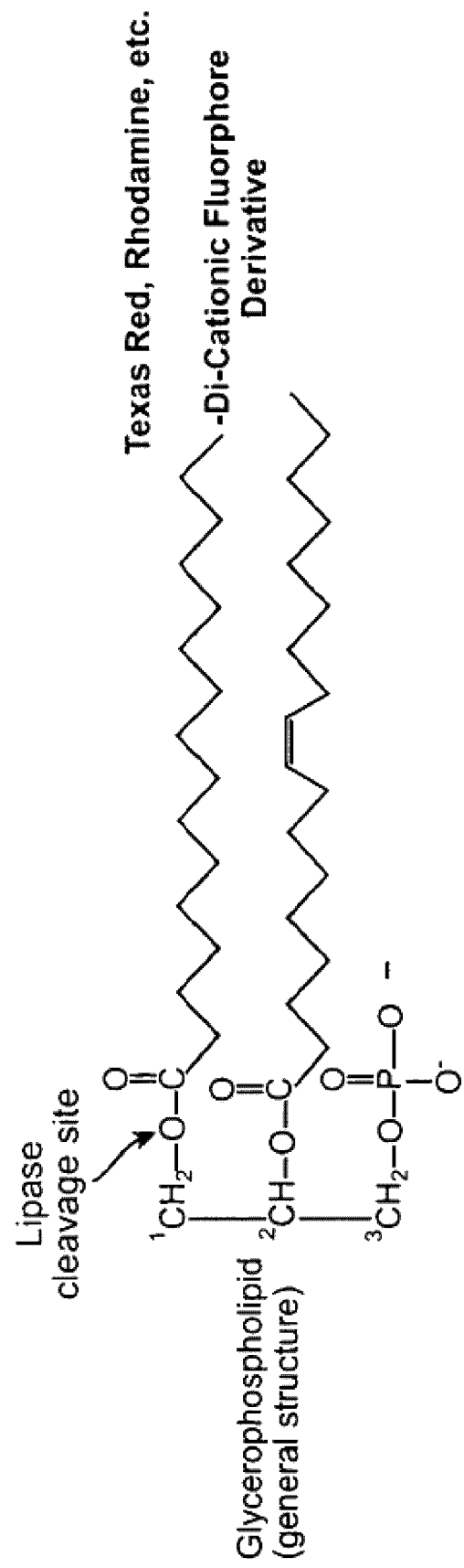
FIG. 10. Design for net charge changing lipase substrate.
Figure 11:
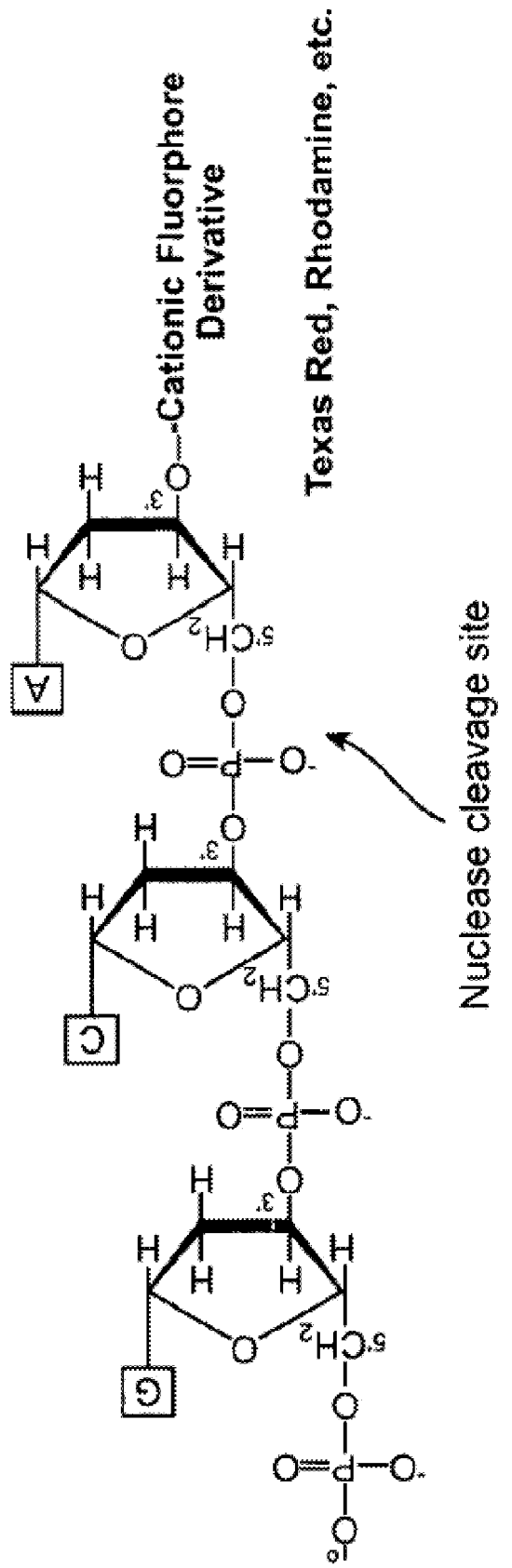
FIG. 11. Design for net charge changing nuclease substrate.

Net charge differentiating substrates for detection of non-protease degradative enzymes directly in blood, plasma and other biological samples are also hereby provided. Like NCDPS, these fluorescent substrates have a net negative or neutral charge prior to cleavage and subsequently produce fluorescently labeled positive-charged cleavage products after cleavage. This specific charge change, for reasons described above, can facilitate in-situ detection in bodily fluids and eliminates the need for sample preparation. To obtain Net Charge Differentiating Amylase Substrates (NCDAS), Net Charge Differentiating Lipid Substrates (NCDLS), and Net Charge Differentiating Nuclease Substrates (NCDNS), and net Charge Differentiating Protein Kinase Substrates (NCDPKS) compounds would be designed and synthesized with the following chemical moieties: a negative charge moiety (with charge Qn), a cleavable substrate moiety (with charge Qs), a positive charge moiety (with charge Qp), and a fluorescent tag (with charge Qf). To obtain a substrate whose net charge is negative prior to cleavage and positive after cleavage, sufficient charge needs to be incorporated in the positive charge and negative charge moieties. For example, if Qf and Qs are zero, then |Qn|>|Qp| would result in the correct net charge change. The generic structures for NCDAS, NCDLS, NCDNS are described below. For amylases, which generally cleave α-1,4 glycosidic bonds, the substrate would have a basic polysaccharide structure with from two to six glucose units to which a positively charge fluorescent group is attached at one end of the structure and a terminal carboxyl group is attached at the other end of the structure producing a neutral substrate. Upon cleavage of the α-1,4 glycosidic bond, a positively charged fluorescent product fragment is produced (see FIG. 9). For lipases, which generally cleave ester bonds in triacylglycerol type structures, the substrates would typically have a basic triacylglcerol structure with one of the fatty acid chains modified with a positively charged fluorophore and one of the glycerol groups modified with a phosphate group producing an overall negatively charged substrate. Upon cleavage of the fatty acid ester bonds a positively charged fluorescent product fragment is produced (see FIG. 10). For nucleases, which generally cleave phosphodiester bonds in polynucleotide structures, the substrate would typically have a basic polynucleotide structures with one of the terminal nucleotides modified with a positively charged fluorophore. Upon cleavage of the phophodiester bonds, a positively charged fluorescent nucleoside fragment is produced (see FIG. 11).

In some embodiments, specific detection of the degradative enzyme is performed. Where the degradative enzyme is specifically detected, the degradative enzyme is detected at a level at least about 2, 3, 4, 5, 10, 10, 30, 40, 50, 100, or 1000 times higher than the level of detection of all other degradative enzymes in the bodily fluid sample. Thus, in some embodiments, the methods provided herein enable specific detection of proteases, lipases, amylases, and nucleases. The specific detection of particular degradative enzymes allows for specific detection of particular disease states as disclosed below.

The NCDPS's and other charge differentiating substrates of this invention may be designed to detect low levels of specific proteolytic enzymes (chymotrypsin, trypsin, matrix metalloproteases, peptidases, thrombin, etc) as well as other enzymes (amylases, lipases, nucleases, kinases etc.) directly in blood, plasma and other biological samples. In some embodiments, the differential in charge between the negatively charged degradative enzyme substrate or neutral degradative enzyme substrate and the positively charged degradative product results in a 10 to 100 fold increase in detection sensitivity.

Figure 5:
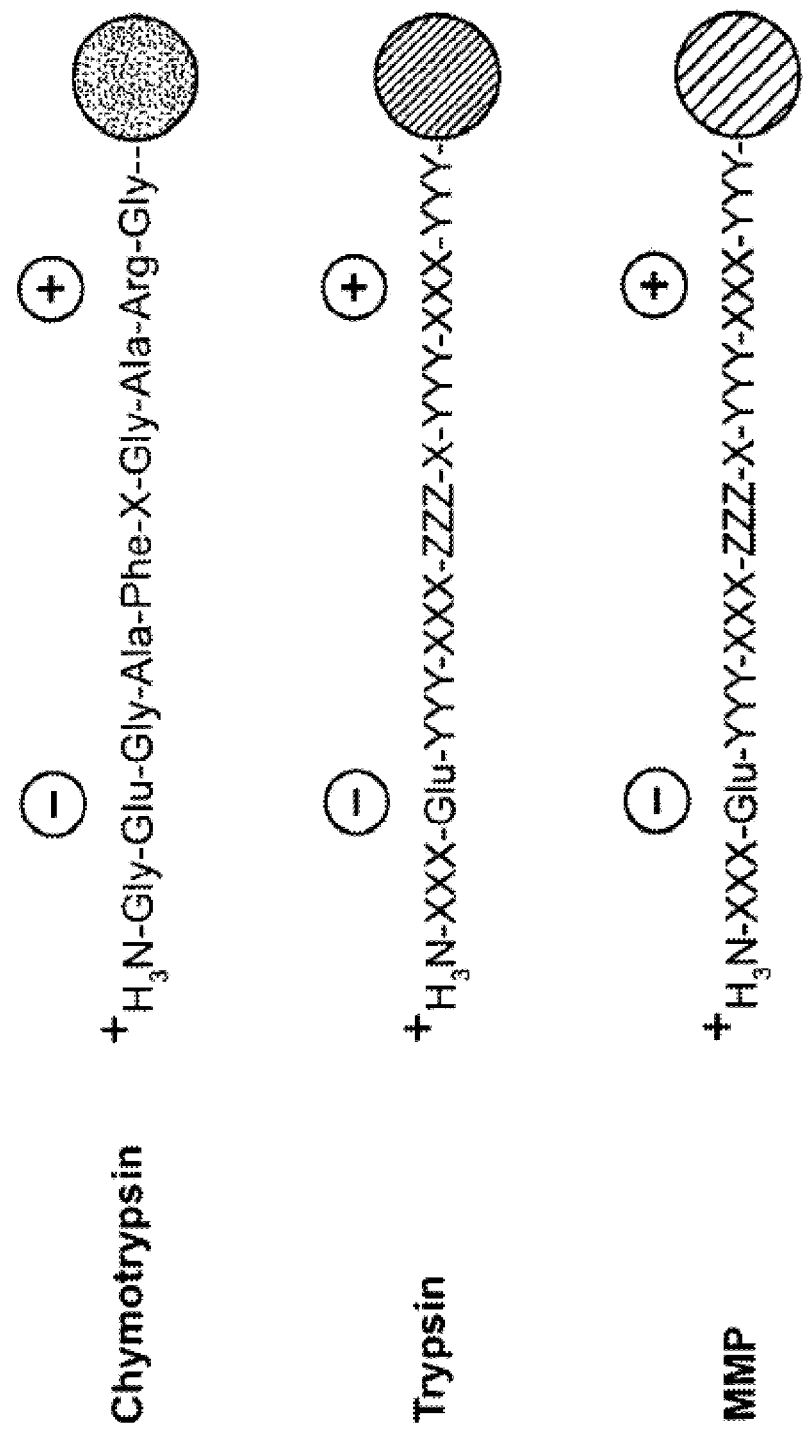
FIG. 5. Peptide substrates for detecting inflammatory cascade enzymes. Each sequence carries cleavage sites at defined locations to promote specific detection. Different fluorescent substrates allow simultaneous detection of multiple enzymes. Sequence: Gly-Glu-Gly-Ala-Phe-Gly-Ala-Arg-Gly (SEQ ID NO:22).

This invention further discloses Multiplex Protease Detection Formats, even where only one particular protease is actually required for diagnostics. Most protease detection systems examine the activity of a single protease, but, as the following discussion will show, a multiplex detection scheme is useful where protease detection is applied to disease diagnostics. A variety of peptide substrates can be designed for inflammatory response or other diseases. Each of the specific enzyme substrate sequences carries a cleavage site at defined location to promote specific detection. Each of the different enzyme substrates is labeled with a different fluorophore (different emission maximum) which allows the simultaneous detection of multiple enzymes (see FIG. 5 and FIG. 6). The cleavage of the peptide substrates will result in a change in the net charge on the complex and the cleaved products can then be separated from the intact peptide substrate by application of a directed electrophoretic field. Subsequent detection is performed with high sensitivity fluorescent detection device which detects the specific fluorescent signals at their different fluorescent emission wavelengths.

In another embodiment, to obtain improved specificity for protease detection, a method is provided to utilize multiple protease substrates preferentially cleaved by different proteases, to more accurately measure the activity of a single target protease. In some embodiments, where the peptide substrates are non-specifically cleaved by other proteases, a protease may be reacted with multiple substrates thereby providing a unique signature of cleavage activity for that group of substrates. This signature distinguishes proteases involved in the cleavage. For example, using only a single chymotrypsin substrate, such as Acetyl-N-Gly-Asp-Ala-Gly-Tyr-/-Ala-Gly-Ala-Gly-Lys(BodipyTR)-NH$_2$ (SEQ ID NO:8), to detect chymotrypsin (which cleaves on the c-terminal side of Tyr, Phe, Trp, and Met) may not account for non-specific cleavage of the substrate by a non-chymotrypsin protease such as elastase (which cleaves on the c-terminal side of Ala, Gly, Val). Using, in addition to the first substrate, a second substrate more specific to elastase, such as Acetyl-N-Asp-Gly-Ala-Val-Gly-Ala-Val-Lys (Bodipy TR)—NH$_2$ (SEQ ID NO:28), it could be concluded that the first cleavage of the substrate may be at least partially attributed to elastase.

In some specific embodiments, the methods provided herein involve the design and synthesis of unique fluorescent/nanoparticle net charge differentiating peptide substrates (NCDPS) (embodiments of the negatively charged degradative enzyme substrate or neutral degradative enzyme substrate) for the highly sensitive and selective detection of the enzymes (proteases, matrix metalloproteases, lipases, amylases) associated with inflammatory cascade in blood or plasma.

Additionally, certain devices disclosed herein allow the product fragments to be rapidly and clearly separated from the blood/plasma components which limit/interfere with detection are also provided. More specifically, substrates which upon cleavage by a specific enzyme, produce cleavage products which have an overall net charge that is different from the original peptide substrate. By way of example, a degradative enzyme substrate with a (0 or −) net charge and a first peptide product with a negative (−) net charge and second fluorescent peptide product with a positive (+) net charge can be rapidly separated by application of an electric field, and then subsequently detected.

Figure 3A:
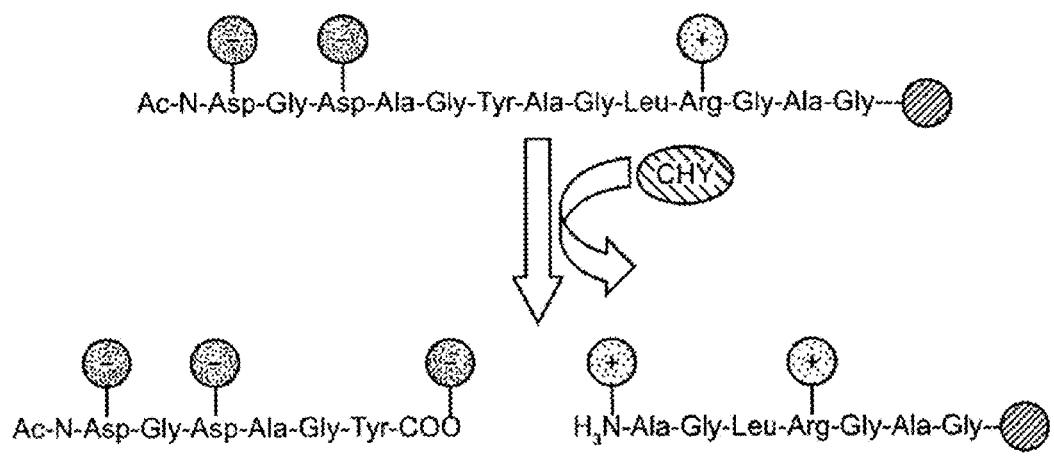
FIGS. 3A-3C. Design and synthesis of the net charge differentiating peptide substrates (NCDPS), cleavage, separation and detection.
Figure 3B:
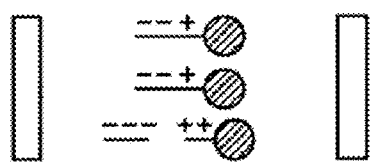
Figure 3C:
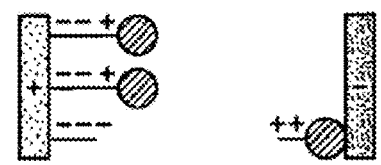

Other embodiments include the development of prototype fluorescent detection systems and ultimately the development of novel diagnostic systems in microtiter plate formats, microarray formats and lab-on α-chip formats for point of care (POC) applications. FIGS. 3A-3C, 4A-4C, 5, 6, 7, 8, 9, 10, and 11 show the design and synthesis of certain fluorescent/nanoparticle net charge differentiating peptide substrates (NCDPS), as well as possible mechanism of NCDPS cleavage, separation and detection in multiplex formats and some other types of NCDPS substrates. The sequence of one NCDPS substrate which was designed and synthesized was Ac-N-Asp-Gly-Asp-Ala-Gly-Tyr-X-Ala-Gly-Leu-X-Arg-Gly-Ala-Gly-diamino-ethyl-Bodipy FL (SEQ ID NO:29). FIG. 3A shows this substrate labeled with a green fluorophore and having a net charge of −1. After reaction with chymotrypsin, two cleavage products are formed. The fluorescently labeled cleavage product has a net charge of +2. FIG. 3B shows a separation scheme without an electric field being applied, where the un-cleaved substrate and cleaved product are unresolved. FIG. 3C shows separation after applying the electric field, where the un-cleaved negatively charged substrate and fluorescently labeled positively charged cleavage product migrate in opposite directions. The fluorescently labeled cleavage product can subsequently be detected with minimal interferences using a sensitive fluorescent detector. This substrate is specific for chymotrypsin and trypsin, and the product fragments have been separated both in whole blood and plasma using agarose gel and/or polyacrylamide gel electrophoresis formats. The detection sensitivity for α-Chymotrypsin in buffer using this substrate was less than 20 mU/mL or <0.3 µg/ml (see Example 2). The detection sensitivity for α-Chymotrypsin in human plasma using this substrate was less than 20 mU/mL or <0.3 µg/ml (see Example 3). The detection sensitivity for α-Chymotrypsin substrate product fragments in rat blood was about 20 mU/mL or ~0.3 µg/ml (see Example 4).

In some embodiments, several novel Fluorescent Net Charge Differentiating Protease Substrates (NCDPS) are provided for the detection of proteases directly in bodily fluid samples including but not limited to blood, plasma, serum, urine, saliva, lymph, semen milk, intestinal and fecal fluids, cerebral spinal fluid, smears and biopsied specimens are hereby disclosed. They are substrates that are specific for α-chymotrypsin, trypsin, elastase, matrix metalloproteinase-2 (MMP-2), MMP-9, MMP-14, and both α-chymotrypsin and trypsin. Prior to cleavage, these fluorescent peptide conjugates are negatively charged. After cleavage by specific proteases, the fluorescently labeled cleavage products are positively charged. Under an electric field, the un-cleaved degradative enzyme substrates and the fluorescently labeled cleavage products will migrate in opposite directions. The fluorescently labeled cleavage products can subsequently be detected by a sensitive fluorescent detector (photomultiplier tube, CCD camera, etc.). Thus, in certain embodiments, these substrates have unique net charge change, from negative to positive upon cleavage, thereby facilitating direct detection of target proteases directly in bodily fluids such as blood and plasma.

Under some conditions it is possible that a particular NCDPS molecule is cleaved non-specifically, and then that molecule can no longer be used to detect the specific protease it was designed for. This may in some cases be an issue for detection of certain proteases in blood, where there is an unusually high level of an endogenous protease activity which interferes with target protease of interest (for example, a high trypsin-like protease background would interfere with trypsin detection if the substrate were susceptible to both enzymes). In order to improve the specificity of detection of a given protease, and facilitate detection in complex bodily fluids such as blood, two methods can used to overcome the problem.

First, the peptide sequence can be improved in order to reduce non-specific cleavage. This may not be as effective, however, for eliminating non-specific cleavage by very non-specific proteases such as elastase. The solution, therefore, is to utilize specific inhibitors together with specific substrates in order to further improve the specificity. These specific inhibitors could reduce non-specific cleavage and facilitate more specific detection directly in blood. For example, to detect chymotrypsin activity specifically, non-specific cleavage by other proteases would need to be greatly reduced if the substrate is susceptible to cleavage by those other proteases. Acetyl-N-Gly-Asp-Ala-Gly-Tyr–/–Ala-Gly-Ala-Gly-Lys (Bodipy TR)-NH2 (SEQ ID NO:8) is a NCDPS for chymotrypsin and would be cleaved on the c-terminal side of Tyr. It potentially can be cleaved by elastase as well since it has several Ala and Gly residues and elastase can cleave on the c-terminal side of Ala and Gly. Thus, in order to improve detection for chymotrypsin in a sample, that sample would be pre-treated with a specific elastase inhibitor such as Glaxo-SmithKline's compound GW311616A. This represents just one example of how a protease inhibitor could be use to improve detection of a specific protease.

IV. Methods of detecting Bodily Fluid Biomolecules using Antibody or Nucleic Acid Probes In another aspect, a method is provided for detecting a biomolecule in a bodily fluid sample. The method includes contacting a bodily fluid sample with a first detection antibody and a second positively charged antibody to form a detectable positively charged biomolecule conjugate. The detectable positively charged biomolecule conjugate is electrophoretically separated from negatively charged endogenous material present in the bodily fluid sample. The detectable positively charged biomolecule conjugate is then detected. The detection of the detectable positively charged biomolecule conjugate is facilitated through detection of the first detection antibody. Biomolecules include, but are not limited to, enzymes, proenzymes, proteins, antibodies, peptides, proteins, protein cleavage sites (from other proteases), peptide cleavage fragments, peptides, hormones, virus, small biomolecules and drug molecules.

Each antibody typically recognizes a distinct epitope site on the biomolecule. In some embodiments, the first detection antibody includes an antibody that is conjugated at the Fc region to a fluorophore or fluorescent protein, polymer or a dendrimer that is sufficiently anionic such that the overall net charge of the antibody-conjugate will be negatively charged or neutral, even when the first detection antibody is bound to its antigen. The second positively charges antibody may include an antibody conjugated at the Fc region to a non-fluorescent polymer, dendrimer or other entities that are sufficiently cationic such that the overall net charge of the detectable positively charged biomolecules conjugate will be positively charged. In some embodiments, the positive charge on the second positively charged antibody exceeds the amount of negative charge on the first detection antibody. After incubation of first detection antibody and the second positively charged antibody with the bodily fluid sample (e.g. a clinical sample containing the biomolecule (or antigen) of interest (e.g. peptide fragment, protein, antibody, disease biomarker)), only biomolecules bound to both the first detection antibody and the second positively charged antibody will migrate toward the cathode under an electric field.

Figure 12:
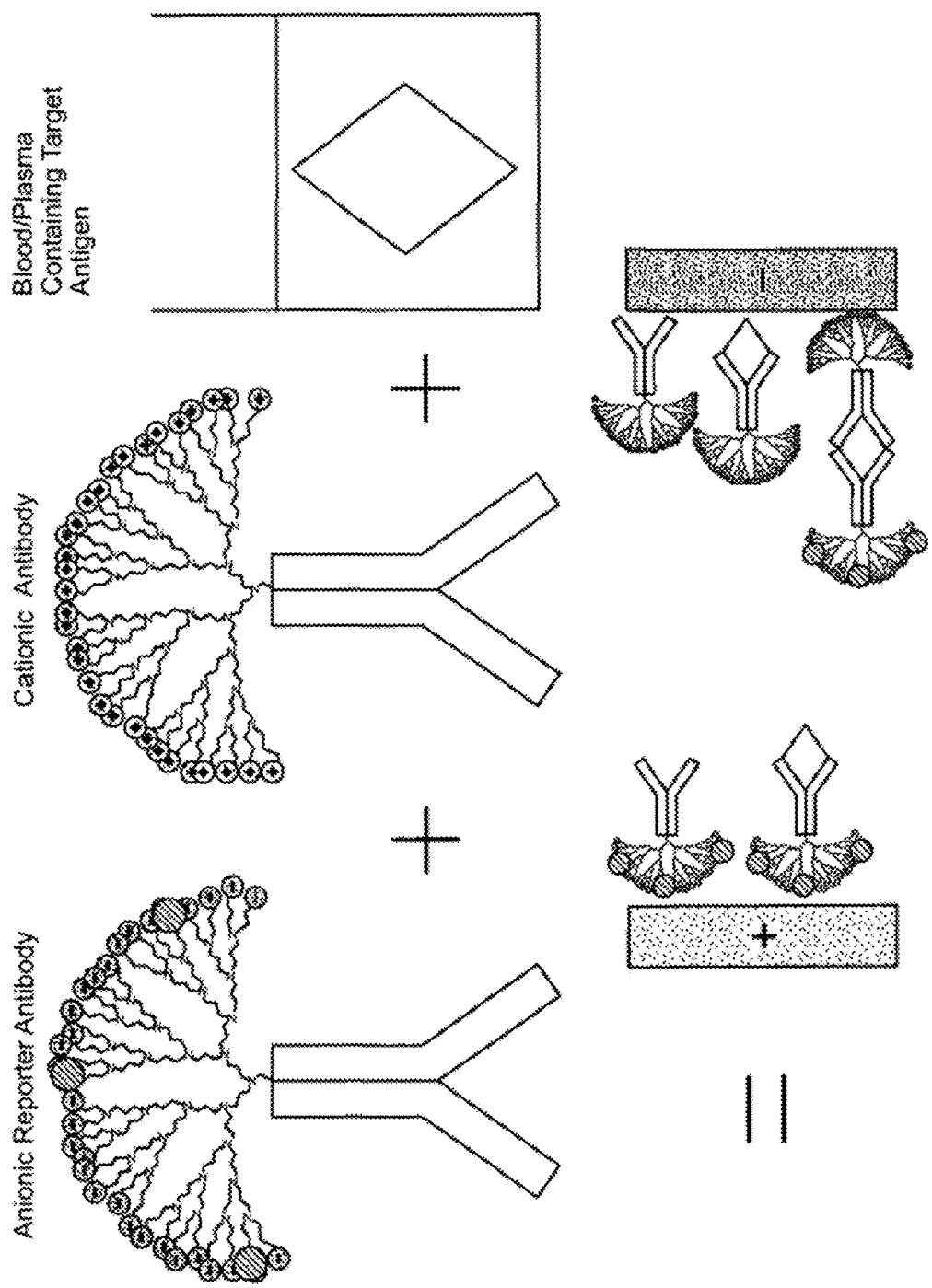
FIG. 12. Scheme for net charge changing double antibody assay.

In some embodiments, as disclosed above, the bodily fluid sample is a blood sample or a blood plasma sample. Components in a blood sample or plasma sample that are negatively charged (e.g. cells, proteins, DNA) will migrate toward the anode. In some embodiments where an electrophoretic gel is employed, components that are much larger than the detectable positively charged biomolecules conjugate (such as cells) do not escape out of the sample loading wells of the gel since they are too large to migrate into the pores of the gel. Thus, in some embodiments using an electrophoretic gel, the fluorescent signal from the detectable positively charged biomolecules conjugate is resolved from many of the background contributors within a bodily fluid sample, which would either remain in the well of the gel or migrate in the opposite direction (see FIG. 12).

As discussed in the background section, recent evidence has shown that one form of insulin resistance may be caused by the proteolytic cleavage of the extracellular α-subunit of the insulin receptor by matrix metalloproteinases (MMPs) [22]. This would cause the release of peptide cleavage fragments in the blood stream. The matrix metalloproteinase MMP-9 cleaves the α-1 insulin receptor site between a glycine and tyrosine residue (-Pro-Glu-Cys-Pro-Ser-Gly↑Tyr-Thr-Met-Asn-Ser-Ser-) (SEQ ID NO:30). This cleavage would release unique peptide fragments into the blood which could be important diabetes biomarkers. Thus, in some embodiments, specific antibodies to α-1 insulin receptor cleavage fragments are designed according to the methods provided herein for use as a diagnostic for diabetes and associated inflammation (see Example 9).

The analog of this process for detecting DNA and mRNA is performed with two nucleic acid probes. The nucleic acid probes may independently be DNA or RNA probes complementary to two sequences of the target DNA or mRNA. Thus, in another aspect, a method is provided for detecting a nucleic acid in a bodily fluid sample. The method includes contacting a bodily fluid sample with a first detection nucleic acid and a second positively charged nucleic acid to form a detectable positively charged nucleic acid conjugate. The detectable positively charged nucleic acid conjugate is electrophoretically separated from negatively charged endogenous material present (e.g. endogenous nucleic acid) in the bodily fluid sample. The detectable positively charged nucleic acid conjugate is the detected. The detection of the detectable positively charged nucleic acid conjugate is facilitated through detection of the first detection antibody.

In some embodiments, the first nucleic acid probe includes a detectable moiety (e.g. covalently or ionically bonded to the nucleic portion) that is negatively charged due to its phosphodiester backbone. In certain embodiments, the second positively charged nucleic acid includes a nucleic acid portion that is conjugated (e.g. covalently or ionically bonded) to a cationic polymer with enough positive charge such that the resulting detectable positively charged nucleic acid conjugate is positively charged. As with the antibody assay described above, the nucleic acid method may be resolved from background contributors in a bodily fluid in an electrophoretic gel.

V. Methods of Diagnosing Disease States

The unique devices, substrates and methods of this invention may be designed to provide both rapid and highly sensitive detection of clinically relevant proteases, lipases, amylases and other shock and inflammatory markers directly in blood and plasma. The ability to detect and monitor these important disease biomarkers directly in blood or plasma provides a number of important advantages. First, sample preparation is costly, time consuming and adds complexity to the overall diagnostic process. Second, sample processing can cause degradation and significant loss of the analyte (specific enzyme), thus reducing the overall sensitivity of the assay. Third, sample processing can add more interfering substances to the final sample, i.e. rupture of blood cells can introduce more non-specific enzymes into the final sample. Fourth, because of sample degradation that occurs when the blood is stored for any length of time before processing, rapid and direct analysis in fresh blood may be important even if the diagnostic result is not needed immediately.

In some embodiments, the disease produces an inflammatory response that is detected using the methods provided herein. In certain embodiments, the inflammatory response and related disease diagnostics is a rapid, quantitative detection for key enzymes (chymotrypsin, trypsin, MMPs, lipases and amylases) in multiplex formats that utilize minimal sample size and with sensitivity sufficient to detect baseline values in control blood or plasma. For chymotrypsin and other proteases, the level of sensitivity may be about 0.1 to 1 IU/mL (<1 µg/ml, pmole-fmole/ml). Substrates and devices that may allow the product fragments to be rapidly and clearly separated from the blood or plasma components, which greatly limit and interfere with the detection of the disclosed substrates. Since these enzymes are the initiates and earlier indicators of shock, inflammation and many other disease processes their detection is important for early warning of shock and monitoring of inflammatory cascades; as well as for diagnosis of chronic inflammatory processes related to diabetes, hypertension, cancer and other diseases.

A. Diagnosis Examples (Statistics)

Protease activities in patient blood or plasma can be modeled by a Gaussian random variable (see FIG. 1A and FIG. 1B). When using these biomarkers for disease diagnosis, an activity threshold must be set to differentiate between the disease and healthy states. When the activity threshold is lowered, a larger range of protease levels or activities are used to diagnose a patient with the disease and the diagnostic sensitivity increases. However, this comes at a cost because there is a trade-off between sensitivity and specificity. As the sensitivity increases, the specificity decreases and more false positives occur. This trade-off becomes quite significant when distinguishing highly overlapping populations. For example, in various studies to determine if MMP-2 and MMP-9 were significantly elevated in patients with type 2-diabetes, there was statistically significant elevation of one or both of those proteases compared to healthy patients ($P<0.05$) [23, 24], but there was also strong overlap in the distributions of MMP-2,9 levels in healthy and diabetic populations. If diabetes were to be diagnosed on MMP-2 or MMP-9 levels alone, the detection would be one of the following: highly specific with no sensitivity, highly sensitive with no specificity, or some compromise in between consisting of poor specificity and poor sensitivity. In order to resolve these strongly overlapping populations, more independent variables such as the activities of additional proteases, are needed to resolve the diseased and healthy populations.

To briefly illustrate this point mathematically, Bayesian detection theory will be employed. Protease detection-based disease diagnosis can be defined as a classification, such that, for a multidimensional vector y of measured information (e.g. activities of multiple proteases), there exists an optimal partition of space $R^n = \{\underline{y}:m(\underline{y})=0\} \cup \{\underline{y}:m(\underline{y})=1\}$, where the probability of false positives PF is minimized, and the probability of detection PD is maximized [25]:

$$m(\underline{y}) = \begin{cases} 1 & \frac{p(\underline{y}|H_1)}{p(\underline{y}|H_0)} \geq \frac{p_0(C_{10}-C_{00})}{p_1(C_{01}-C_{11})} \\ 0 & \frac{p(\underline{y}|H_1)}{p(\underline{y}|H_0)} < \frac{p_0(C_{10}-C_{00})}{p_1(C_{01}-C_{11})} \end{cases}$$

$C_{10}$ represents the cost of choosing hypothesis $H_1$ (e.g. patient has diabetes) when the true state was $H_0$ (e.g. patient does not have diabetes), etc. The a priori probabilities p0, p1 are perhaps unavailable for general cases, but can be estimated for certain cases. The costs may also be adjusted towards the particular clinical situation, where a false positive may be less injurious than a false negative. Now, for a set of independent variables, the false detection probabilities become the product of the conditional probabilities in each dimension. Therefore, if a diagnosis is based on more independent variables, there will be a higher likelihood of proper diagnosis (see FIG. 2). If independent variables are unavailable, then minimally correlated dimensions would be preferable. By monitoring the activities of multiple proteases in the blood, multiplex detection schemes maintain both high sensitivity and specificity.

VI. Kits

In another aspect, kits are provided that typically provide a convenient means for supplying necessary reagents for the methods described above, such as ancillary reagents, apparatuses, instructions and/or other components necessary to implement the invention.

For example, in one embodiment, a kit for detecting a degradative enzyme in a bodily fluid sample (e.g. crude bodily fluid sample) is provided. The kit includes a negatively charged degradative enzyme substrate or neutral degradative enzyme substrate. In some embodiments, the kit includes an electrophoretic separation apparatus. In some embodiments, the electrophoretic separation apparatus is a gradient gel. In other embodiments, the kit further includes a detector. In some embodiments, the detector is an epifluorescence detector. In other embodiments, the degradative enzyme is a protease, a lipase, an amylase or a nuclease. In one embodiment, the degradative enzyme is a protease. In some embodiments, the negatively charged degradative enzyme substrate or neutral degradative enzyme substrate is a peptide, a lipid, a polysaccharide or a nucleic acid. In some embodiments, the negatively charged degradative enzyme substrate or neutral degradative enzyme substrate is a peptide. In another embodiment, the crude bodily fluid sample is a crude blood sample or a crude lymphoid fluid sample. In some embodiments, the crude bodily fluid sample is a crude blood sample. Similar kits may also be provided for the methods of detecting biomolecules and diagnosing diseases described above.

Other materials useful in the performance of the assays can also be included in the kit, including test tubes, transfer pipettes, and the like. The kit may also include written instructions for the use of one or more of the reagents described herein. The invention contemplates additional kits packaged to deliver, instruct and otherwise aid the practitioner in the use of the invention. These additional kits include those for the use of diagnostic embodiments of the invention, and their construction is well known by those of skill in the art provided with the reagents set forth herein.

The characteristics of the components of the methods described above are equally applicable to the kits provided herein.

VII. EXAMPLES

A major advantage in some embodiments of the methods provided herein is the novel protease substrates (NCDPS) which can be used directly in blood or plasma. This is demonstrated in the following experimental examples.

FIGS. 1A-28 disclose, inter alia, the design and synthesis of certain unique fluorescent net charge differentiating peptide substrates (NCDPS); certain embodiments of NCDPS cleavage, separation and detection; the design of certain embodiments of detection/separation devices and systems for using NCDPS substrates bioanalytical and diagnostic assays; and experimental results using certain NCDPS substrates.

Example 1

Electrophoretic Mobility of Streptavidin Quantum Dot—Biotinyl-Gln-His-Trp-Ser-Tyr-Gly-Leu-Arg-Pro-Gly-NH2 Derivative This represents an initial experiment where a biotinylated peptide (Biotin-Gln-His-Trp-Ser-Tyr-Gly-Leu-Arg-Pro-Gly-NH2, SEQ ID NO:24) was attached to red fluorescent streptavidin quantum dots and the relative changes in electrophoretic mobility were observed. The overall results demonstrated a significant charge reduction (less negative) for Q-dots which have been derivatized with the peptide (see FIG. 19). Sample 1 (0:1 Subst:Qdot) Control=3 uL Qdot 565 40 nM/0.5×TBE+3 uL 80 mM Tris HCL pH 7.8. Sample 2 (1:1 Subst:Qdot)=3 uL Qdot 565 40 nM/0.5×TBE+3 uL peptide 40 nM/80 mM Tris HCL pH 7.8. Sample 3 (10:1 Subst:Qdot)=3 uL Qdot 565 40 nM/0.5×TBE+3 uL peptide 4 00 nM/80 mM Tris HCL pH 7.8. Sample 4 (100:1 Subst:Qdot)=3 uL Qdot 565 40 nM/0.5×TBE+3 uL peptide 4 uM/80 mM Tris HCL pH 7.8. Sample 5 (1000:1 Subst:Qdot)=3 uL Qdot 565 40 nM/0.5×TBE+3 uL peptide 40 uM/80 mM Tris HCL pH 7.8. Sample 6 (10000:1 Subst:Qdot)=3 uL Qdot 565 40 nM/0.5×TBE+3 uL peptide 400 uM/80 mM Tris HCL pH 7.8. Again, the overall results show that a positively charged peptide sequences can be designed which markedly influences the electrophoretic mobility of fluorescent nanoparticles. However, even thought there were multiple peptides on the quantum dot, the overall particle polarity could not actually be reversed. These results help in determining the level of charge a peptide would need to have, in order to cause quantum dot to reverse charge.

Example 2

Figure 20:
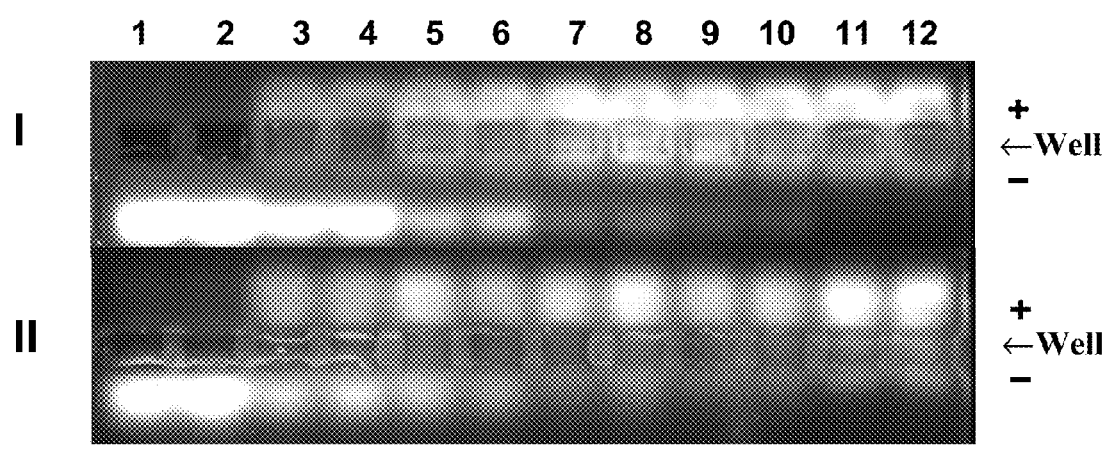
FIG. 20. Electrophoretic separation of α-chymotrypsin and trypsin in 1×PBS buffer using a NCDPS (Example 2).
Figure 21:
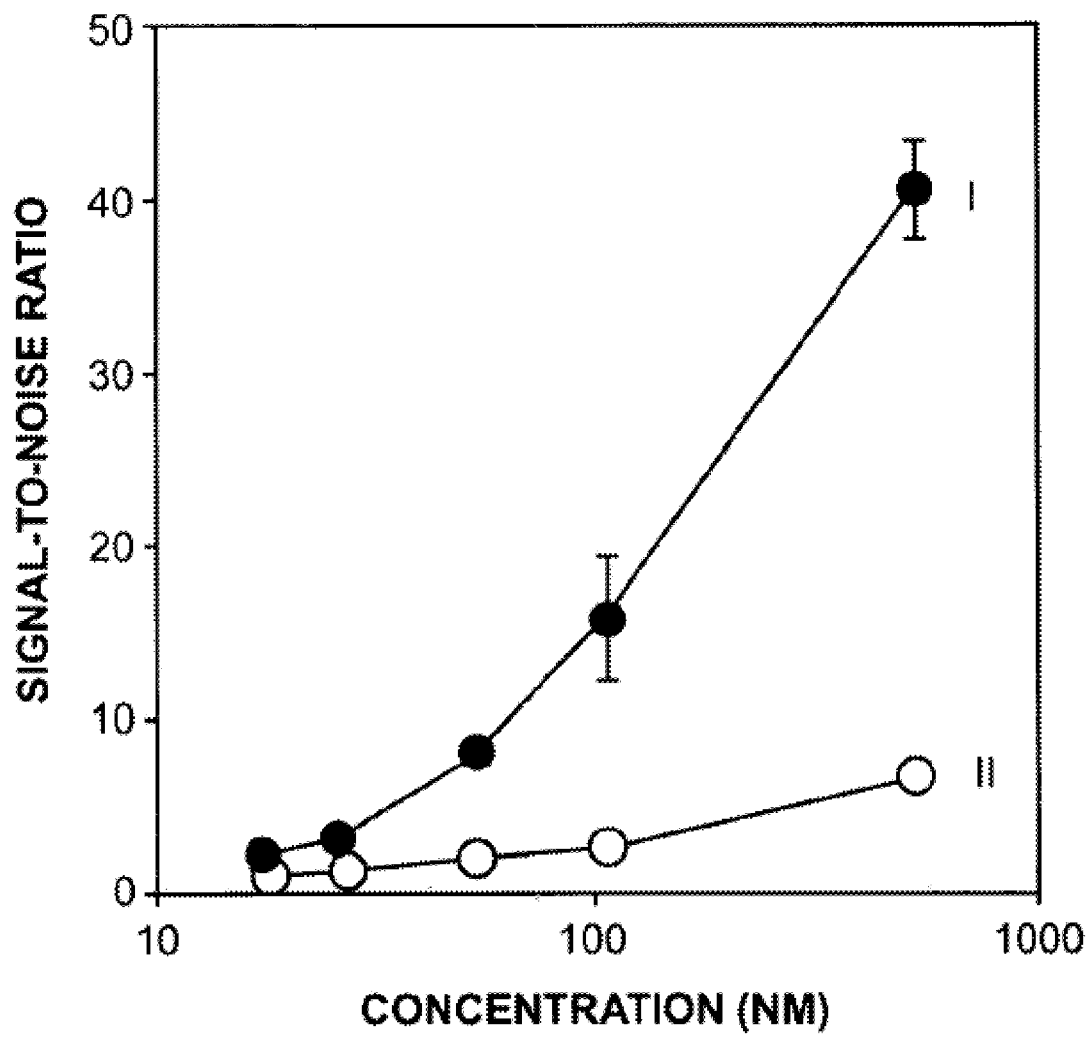
FIG. 21. Enzyme activity standard curves for detection of α-chymotrypsin and trypsin in 1×PBS buffer using a NCDPS (Example 2).

Detection of Pancreatic α-Chymotrypsin and Pancreatic Trypsin in 1×PBS Buffer Using a Net Charge Differentiating Peptide Substrate In this experiment a 1 mg/ml (650 µM) stock solution of the NCDPS substrate Ac-N-Asp-Gly-Asp-Ala-Gly-Tyr-Ala-Gly-Leu-Arg-Gly-Ala-Gly-diamino-ethyl-Bodipy FL (SEQ ID NO:29) (MW 1537.4) was prepared by dissolving the peptide in 1× phosphate buffered saline (PBS) at pH 7.8. Stock solutions from lyophilized bovine pancreatic α-chymotrypsin (MW 25 kDa) and bovine pancreatic trypsin (MW 23.8 kDa) were prepared at 2 mg/ml (80 µM α-chymotrypsin and 84 µM trypsin) concentrations in 1 mM HCl. Both proteases were serially diluted in 1 mM HCl in order to obtain the desired concentrations. A solution of 486 µg/ml (316 µM) of the Ac-N-Asp-Gly-Asp-Ala-Gly-Tyr-Ala-Gly-Leu-Arg-Gly-Ala-Gly-diamino-ethyl-Bodipy FL peptide was prepared in 1×PBS (pH 7.8). Aliquots of 14.4 µl of the DCDPS peptide solution (1×PBS) were mixed with 1 µl aliquots of various concentrations of the proteases or 1 µl of 1 mM HCl for the negative control, and then allowed to react for one hour. 6 µl samples containing 3 µg (300 µM) of the substrate with protease concentrations ranging from 500 nM (lanes 1-2), 100 nM (lanes 3-4), 50 nM (lanes 5-6), 30 nM (lanes 7-8), 20 nM (lanes 9-10) or 0 nM (lanes 11-12) were loaded into the wells of a 4% high resolution agarose gel run in 0.5×TBE. The samples were electrophoresed at 80 V for 0.5 hr and then visualized directly by a BioDoc-It® System with a Model M-26 transilluminator (UVP, Upland, Calif.) at an excitation of 302 nm and through a SYBR® Green filter (passing 500-580 nm with peak transmission of 90% at 540 nm). The gel results are shown in FIG. 20, and by inspection indicate a detection level of about 20 nM for chymotrypsin and about 30 nM for trypsin in 1×PBS. Gels were then quantified with a Storm 480 gel scanner using ImageQuant v5.2 (Molecular Dynamics, Sunnyvale, Calif.) (fluorescence mode, high sensitivity, 100 µm pixel size, 1000V photomultiplier tube) with a 450 nm excitation filter and a 520 nm long pass emission filter. The plotted results which are presented in FIG. 21 gave a detection limit of about 10 nM (0.02 activity units[1]/ml) for α-chymotrypsin and 20 nM (8 activity units/ml) for trypsin in 1×PBS.

Example 3

Detection of Pancreatic α-Chymotrypsin and Pancreatic Trypsin in Human Plasma Using a Net Charge Differentiating Peptide Substrate In this example a 1 mg/ml (650 µM) stock solution of the peptide substrate was prepared from lyophilized Ac-N-Asp-Gly-Asp-Ala-Gly-Tyr-Ala-Gly-Leu-Arg-Gly-Ala-Gly-di-amino-ethyl-Bodipy FL (MW 1537.4) (SEQ ID NO:29) by dissolving the peptide in 1×PBS at pH 7.8. Stock solutions from lyophilized bovine pancreatic α-chymotrypsin (MW 25 kDa) and bovine pancreatic trypsin (MW 23.8 kDa) were prepared at 2 mg/ml (80 µM α-chymotrypsin and 84 µM trypsin) concentrations in 1 mM HCl. Both proteases were serially diluted in 1 mM HCl in order to obtain the desired concentrations. A solution of 486 µg/ml (316 µM) of the Ac-N-Asp-Gly-Asp-Ala-Gly-Tyr-Ala-Gly-Leu-Arg-Gly-Ala-Gly-diamino-ethyl-Bodipy FL peptide was prepared in un-diluted human plasma. Aliquots of 14.4 µl of the peptide plasma solution were mixed with 1 µl aliquots of various concentrations of the proteases or 1 ul of 1 mM HCl for the negative control and then allowed to react for one hour.

Figure 22:
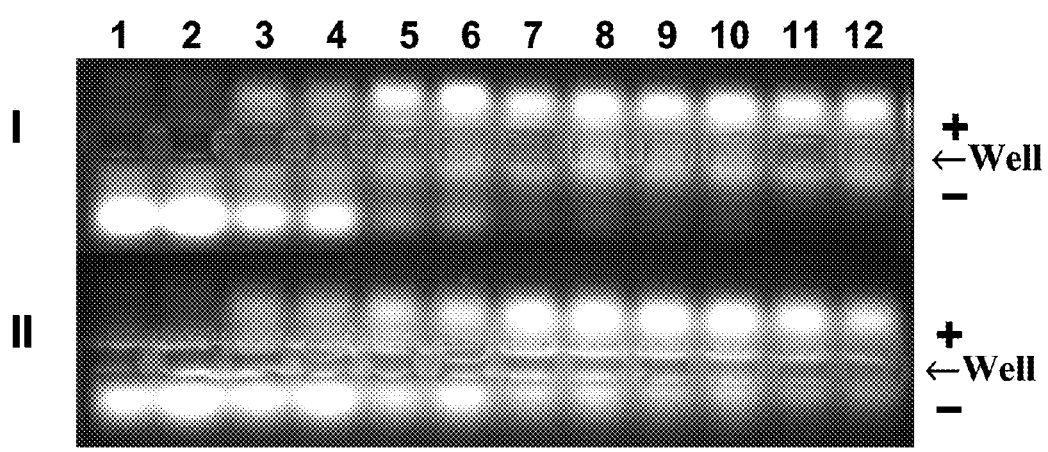
FIG. 22. Electrophoretic separation of α-chymotrypsin and trypsin in human plasma using a NCDPS (Example 3).
Figure 23:
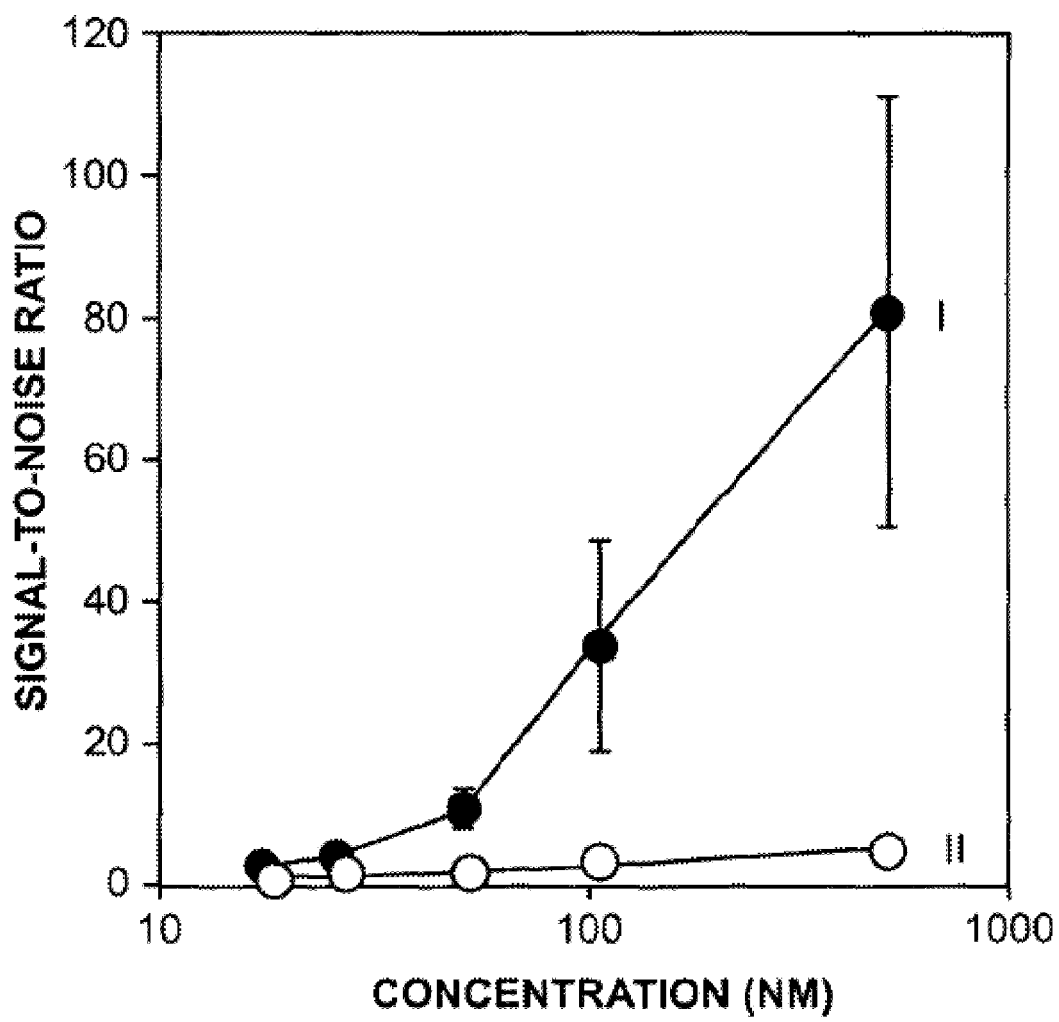
FIG. 23. Enzyme activity standard curves for detection of α-chymotrypsin and trypsin in human plasma using a NCDPS (Example 3).

Samples of about 6 µl each containing 3 µg (300 µM) of the substrate with protease concentrations that ranged from 500 nM (lanes 1-2), 100 nM (lanes 3-4), 50 nM (lanes 5-6), 30 nM (lanes 7-8), 20 nM (lanes 9-10) or 0 nM (lanes 11-12) were loaded into the wells of a 4% high resolution agarose gel in 0.5×TBE. The samples were electrophoresed at 80 V for 0.5 hr and then visualized directly by a BioDoc-It® System with a Model M-26 transilluminator (UVP, Upland, Calif.) at an excitation of 302 nm and through a SYBR® Green filter (passing 500-580 nm with peak transmission of 90% at 540 nm). The gel results are shown in FIG. 22, and indicated by inspection a detection level of about 20 nM for chymotrypsin and about 20 nM for trypsin in plasma. Gels were then quantified with a Storm 480 gel scanner using ImageQuant v5.2 (Molecular Dynamics, Sunnyvale, Calif.) (fluorescence mode, high sensitivity, 100 µm pixel size, 1000V photomultiplier tube) with a 450 nm excitation filter and a 520 nm long pass emission filter. The plotted results which are presented in FIG. 23 give a detection limit of about 10 nM (0.02 activity units[1]/ml) for α-chymotrypsin and 20 nM (8 activity units/ml) for trypsin in 1× plasma.

Example 4

Detection of NCDPS Chymotrypsin and Trypsin Cleavage Fragments in Whole Blood

Figure 24:
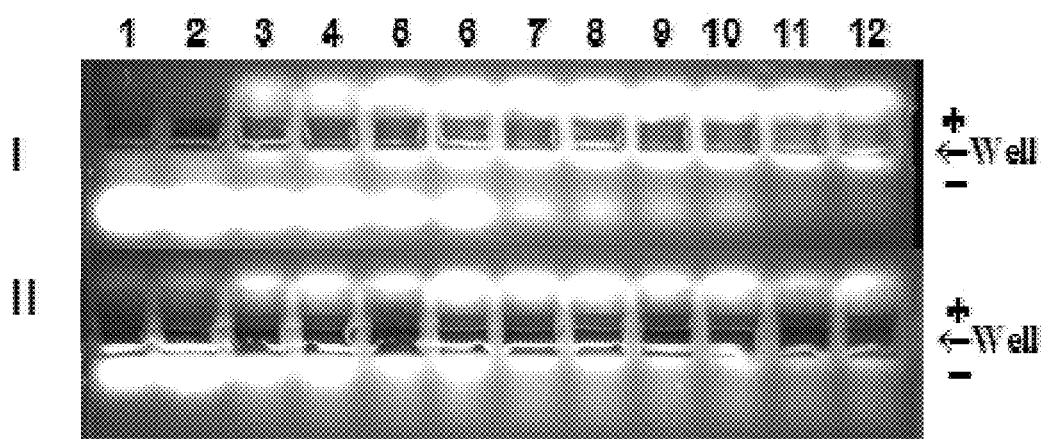
FIG. 24. Agarose gel electrophoresis patterns of α-chymotrypsin (gel I) and trypsin (gel II) cleavage products in whole rat blood (Example 4).
Figure 25:
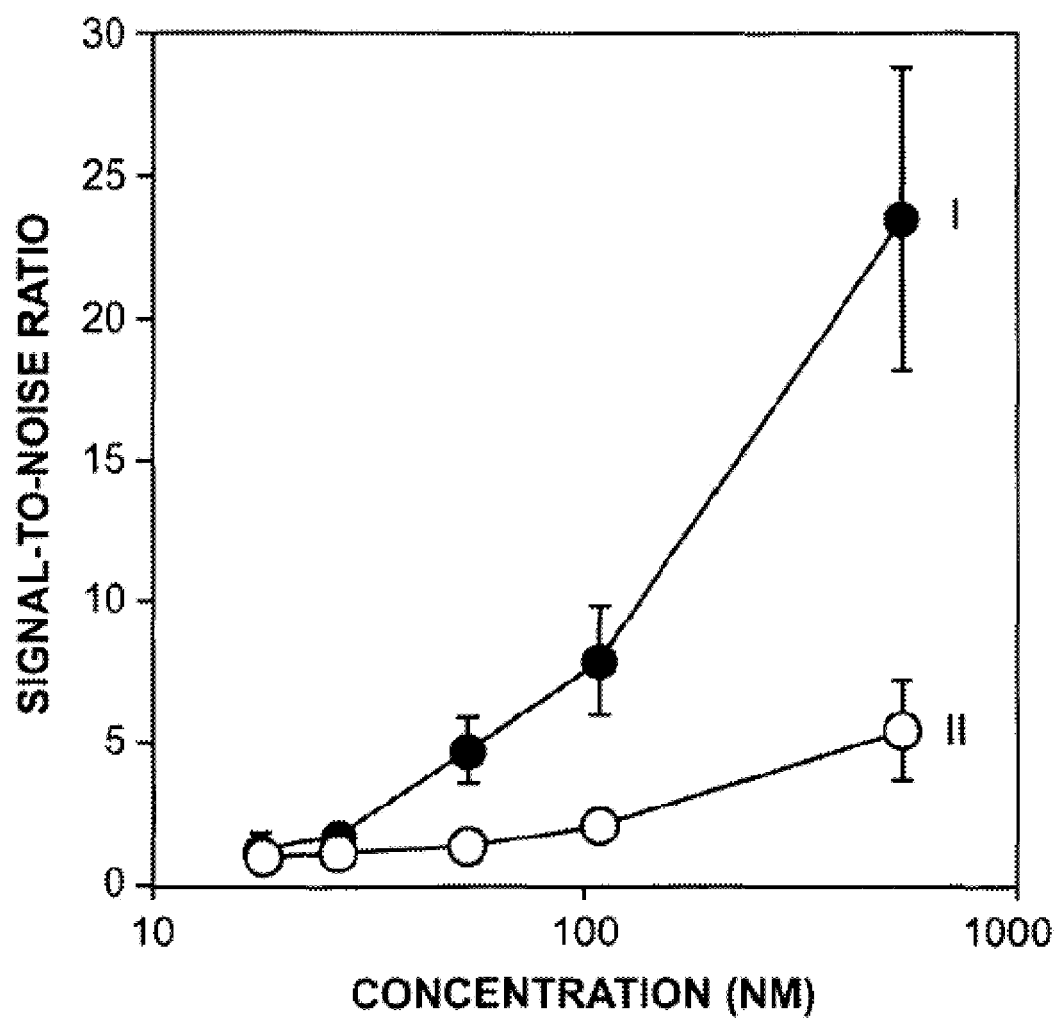
FIG. 25. Enzyme activity standard curves generated from the detection of α-chymotrypsin (curve I) and trypsin (curve II) cleavage products in whole rat blood (Example 4).
Figure 26:
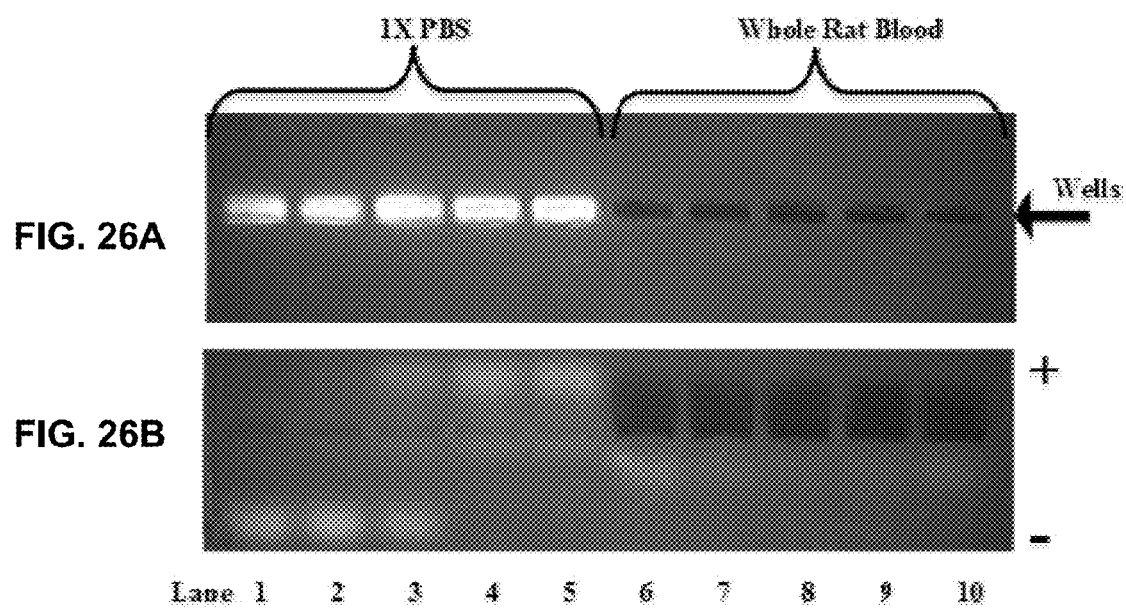
FIGS. 26A-26B. Electrophoretic pattern of the Acetyl-N-Asp-Gly-Asp-Ala-Gly-Tyr-/-Ala-Gly-Leu-/-Arg-/-Gly-Ala-Gly-Bodipy FL (SEQ ID NO:25) reacted with bovine pancreatic alpha-chymotrypsin in 1×PBS (left half) and whole rat blood (right half). Legend.

A 1 mg/ml stock solution of Ac-N-Asp-Gly-Asp-Ala-Gly-Tyr-Ala-Gly-Leu-Arg-Gly-Ala-Gly-diamino-ethyl-Bodipy FL (SEQ ID NO:29) peptide substrate and various concentrations (2 mg/ml stock solution and serial dilutions of stock) of bovine pancreatic α-chymotrypsin and trypsin were prepared in the manner described in the above examples. For detection of the cleavage products from reaction with α-chymotrypsin, a solution of 486 µg/ml (316 µM) of the Ac-N-Asp-Gly-Asp-Ala-Gly-Tyr-Ala-Gly-Leu-Arg-Gly-Ala-Gly-diamino-ethyl-Bodip peptide was prepared in 1×PBS, pH 7.8. In individual reaction tubes, 14.4 µl aliquots of this peptide solution was mixed with 0.5 µl aliquots of various concentrations of α-chymotrypsin (500 nM, 100 nM, 50 nM, 30 nM, 20 nM or 0 nM) and then allowed to react for 1 hour. Heparinized whole rat blood was treated with an equal volume of 10× protease inhibitor cocktail and allowed to incubate for 1 minute. Each 14.9 µl reaction mixture of enzyme and substrate was then mixed with 7 µl of protease inhibitor-treated blood, forming a mixture containing 16% (v/v) blood. Immediately after mixing the treated blood with the reaction mixture, 6 µl of each sample was loaded into the wells of a 4% high-resolution agarose gel (0.5×TBE) and electrophoresed at 80 V for 0.5 hour. The gels were visualized and quantified as was described in the above examples. For detection of the cleavage products by trypsin, a solution of 486 µg/ml (316 µM) of the Ac-N-Asp-Gly-Asp-Ala-Gly-Tyr-Ala-Gly-Leu-Arg-Gly-Ala-Gly-diamino-ethyl-Bodipy FL peptide was prepared in 1×PBS at pH 7.8. In individual reaction tubes, 7.2 µl aliquots of this peptide solution was mixed with 0.5 µl aliquots of various concentrations of trypsin (500 nM, 100 nM, 50 nM, 30 nM, 20 nM or 0 nM) and then allowed to react for 1 hour. Heparinized whole rat blood was treated with 10× protease inhibitor cocktail as before and each 7.7 µl reaction mixture was mixed with 7 µl of protease inhibitor-treated blood, forming a final solution containing 24% (v/v) blood. Immediately after mixing the treated blood with the reaction mixture, samples were electrophoresed, visualized, and then quantified as described above. The gel results for both chymotrypsin and trypsin are shown in FIG. 24, and give by inspection a an estimated detection limit of 20 nM (0.03 activity units[1]/ml) for α-chymotrypsin and 50 nM (10 activity units[2]/ml) for trypsin. FIG. 25 shows the plotted results and also gives give by inspection a detection limit of 20 nM (0.03 activity units[1]/ml) for α-chymotrypsin and 50 nM (10 activity units[2]/ml) for trypsin in blood.

Example 5

Detection of Chymotrypsin/Trypsin Activity in Whole Blood Using NCDPS Substrate

In this experiment 7 µl of 1× phosphate buffered saline (PBS) at pH 7.8 or 7 µl of whole rat blood were mixed with the following: 7 µl of 1 mg/ml Acetyl-N-Asp-Gly-Asp-Ala-Gly-Tyr-Ala-Gly-Leu-Arg-Gly-Ala-Gly-Bodipy FL (SEQ ID NO:26) in 1×PBS pH 7.8; 0.4 µl of 2 M $CaCl_2$; and 0.5 µl of the following concentrations 2 mg/ml, 0.4 mg/ml, 0.08 mg/ml and 0 mg/ml of human pancreatic α-chymotrypsin. The mixtures were incubated for 1 hour and then 6 µl of sample was loaded into the wells of a 4% high resolution agarose gel. The five wells on the left-hand side were loaded with 1×PBS samples and the five wells on the right right-hand side were loaded with the whole rat blood samples. Electrophoresis was performed for 30 minutes at 80 V and then the gel was imaged using a BioDoc-It® System with a Model M-26 transilluminator (UVP, Upland, Calif.). Results for the experiment are shown in FIG. 26A and FIG. 26B. The upper FIG. 26A show the gel before the electric field was applied and the quenching of fluorescent signal from NCDPS substrate by the blood samples can clearly be seen in the five wells on the left side. This sensitivity-reducing quenching issue would occur for many of the current types of fluorescent enzyme assays utilizing classical fluorogenic substrates. As a result, these latter methods typically require considerable sample preparation, which is time-consuming and makes the measurements less accurate, in order to recover fluorescent signal. The lower FIG. 26B shows the appearance of cleavage products in the first three 1×PBS samples and in the blood samples. The results demonstrate the rapid separation of fluorescent signal from blood and subsequent recovery (un-quenching) of fluorescent signal eliminating the need for sample preparation.

Example 6

Figure 27:
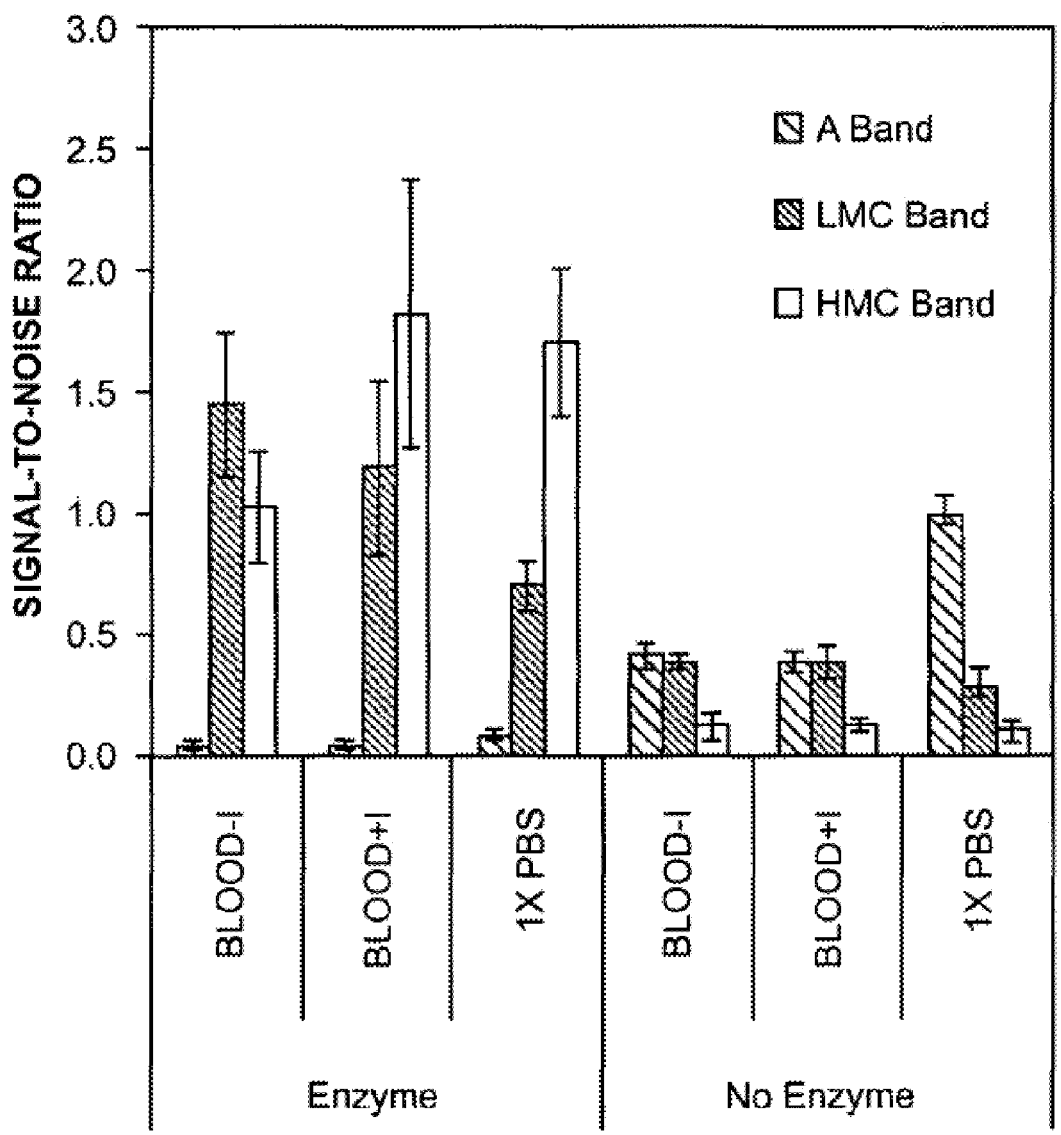
FIG. 27. Non-specific binding activity of the NCDPS substrate.
Figure 28:
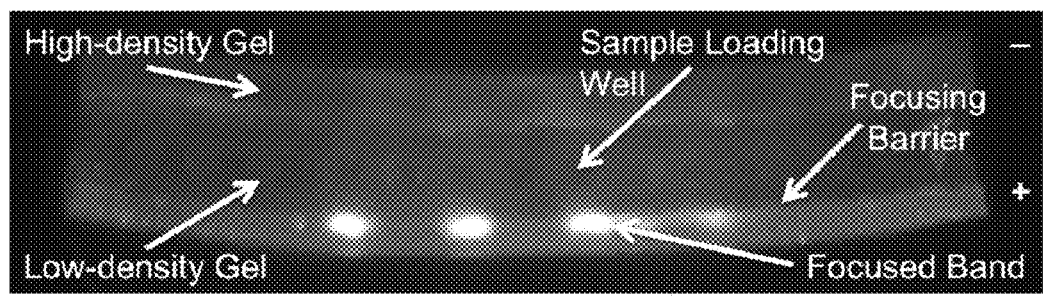
FIG. 28. Stacking gel focusing of the NCDPS substrate.

Determination of Non-Specific Binding of Pancreatic α-Chymotrypsin/Trypsin Net Charge Differentiating Substrate A 1 mg/ml solution of the substrate Ac-N-Asp-Gly-Asp-Ala-Gly-Tyr-Ala-Gly-Leu-Arg-Gly-Ala-Gly-diamino-ethyl-Bodipy FL (MW 1537.4) (SEQ ID NO:29) was prepared in 1×PBS, pH 7.8 and 7 µl aliquots of this solution were then each mixed with 1 µl of either 2 mg/ml bovine pancreatic α-chymotrypsin or 1 mM HCl, as a negative control. This reaction was allowed to proceed for 1 hour. Rat blood was obtained as before and half of it was treated with an equal volume of 10× protease inhibitor cocktail, while the other half was mixed with an equal volume of 1×PBS, pH 7.8. To each 8 µl solution of substrate (with or without α-chymotrypsin added), 14 µl of either untreated rat blood, protease inhibitor-treated rat blood, or 1×PBS, pH 7.8 was added and gently mixed. For samples with blood added, the final concentration of blood was 32% (v/v). Samples were then electrophoresed and visualized in the same way as described above. In order to compare data from both gels, the samples containing only peptide in 1×PBS were split between the two gels as a control. The results in FIG. 27 show that the uncleaved substrate in 1×PBS (unreacted with enzyme) that had migrated toward the anode as a single band (see FIG. 27, No Enyzme—1×PBS—A band), now, after cleavage by α-chymotrypsin, migrates as two bands toward the cathode, representing a primary (see FIG. 27, Enzyme—1×PBS—HMC band) and a secondary (see FIG. 27, Enzyme—1×PBS—LMC band) α-chymotrypsin cleavage product. Comparing the reactions in 1×PBS (see FIG. 27, Enzyme/No Enzyme—1×PBS—LMC/HMC bands) with the reactions in protease inhibitor treated-blood (see FIG. 27, Enzyme/No Enzyme—BLOOD+I–LMC/HMC bands), with and without α-chymotrypsin added, the data shows that there was no significant shift up or down of the SNR from the cathodic bands. If there was significant non-specific binding altering the net charge of the uncleaved substrate or of the fluorescently labeled cleavage products, then there should be a significant shift of the SNR of those bands. Therefore, this data shows that non-specific binding is not occurring to any significant degree and hence does not affect the accuracy of this detection scheme.

Example 7

Stacking Gel-Based Concentration of a Net Charge Differentiating Protease Substrates to Improve Sensitivity A discontinuous gel was used in order to demonstrate a focusing of the α-chymotrypsin/tryspin substrate Ac-N-Asp-Gly-Asp-Ala-Gly-Tyr-Ala-Gly-Leu-Arg-Gly-Ala-Gly-di-amino-ethyl-Bodipy FL (SEQ ID NO:29). A 7 mm wide 1% agarose gel surrounded by 2 mm wide 20% T, 5% C polyacrylamide gels was created, with 0.5×TBE used for both the gel casting buffer and running buffer. Samples of 0.5 mg/ml substrate in 0.5×TBE were loaded, in 6 µl aliquots, into wells formed in the polyacrylamide gel and then electrophoreses at 300 V for 10 minutes in order to get the substrate to reach the barrier between the two types of gel and focus. The results, shown in FIG. 28 demonstrate that after 10 minutes the substrate migrated from the sample loading well, through a lower-density into higher-porosity agarose gel and then concentrated upon reaching a lower-porosity barrier formed by a higher-density polyacrylamide gel.

Example 8

Figure 29:
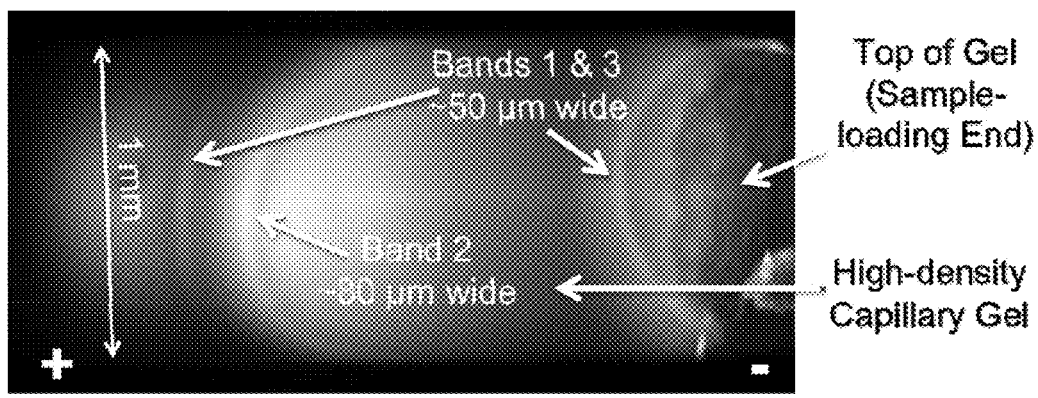
FIG. 29. High density capillary gel format for focusing the NCDPS substrate.

High Voltage Electrophoresis in a High-Density Polyacrylamide Capillary Gel to Focus NCDPS to Improve Sensitivity To a 1 mm O.D. capillary filled with 2 cm of a 26% T, 8% C polyacrylamide gel in 0.5×TBE, a 2 µl sample of 0.3 mg/ml of the Ac-N-Asp-Gly-Asp-Ala-Gly-Tyr-Ala-Gly-Leu-Arg-Gly-Ala-Gly-diamino-ethyl-Bodipy FL (SEQ ID NO:29) substrate was applied. In a running buffer of 0.5×TBE electrophoresis was performed at 200 V (10 V/mm) for 5 minutes. Imaging was performed with an epifluorescent microscope with a 2.5×, 0.07 NA Objective, a Bodipy TR Filter Set, and a Peltier thermal controlled Hamamatsu Orca-ER CCD camera. The results, shown in FIG. 29, demonstrate high concentration and focusing of the fluorescent substrate into 50 µm and 80 µm-wide bands after 5 minutes of electrophoresis. The 2 µl sample volume injected into the 1 mm diameter capillary spans approximately a 2.5 mm length of capillary, before the electric field was applied. Therefore, this concentration of the fluorescent signal into the two bands, totaling 130 µm of capillary length, represents more than a 20 fold concentration of the signal.

Example 9

Detection of α-1 Insulin Receptor Cleavage Fragments in Blood Using a Charge Changing Antibody Assay In this example the net charge changing antibody method is used for the detection of α-1 insulin receptor peptide cleavage fragments (from MMP-9) directly in a whole blood sample. Into a 50 ul blood sample is added a 10 ul aliquot (1×TBE buffer, pH 7.8) containing fluorescent (Ex 490 nm and Em 510 nm) antibody 1 (for α-1 insulin receptor peptide cleavage fragment epitope A) at 100 ng/ml, and the non-fluorescent cationic antibody 2 (for α-1 insulin receptor peptide cleavage fragment epitope B) at 100 ng/ml. The patient or test samples along with a negative control (normal blood) are allowed to react for about 15 minutes, and then 10 ul of each sample is placed into the sample chamber of the focusing gel device. A DC electric field at 200 volts is now applied to the system for about five minutes. After the separation has been achieved the anode (negative electrode) side of the focusing gel is scanned with an epifluorescent detector and the fluorescent signals (at 510 nm) for the samples and control are detected and analyzed. The presence of any clinically relevant amounts of the α-1 insulin receptor peptide cleavage fragments in the patient/test samples produces a higher fluorescent signal, and indicates the presence of MMP-9 which is diagnostic for diabetes and associated inflammation.

VIII. REFERENCES

1. Schmid-Schönbein, G. W. and T. E. Hugli, A new hypothesis for microvascular inflammation in shock and multiorgan failure: self-digestion by pancreatic enzymes. Microcirculation, 2005. 12(1): p. 71-82.
2. Waxman, K., Shock: ischemia, reperfusion, and inflammation. New Horiz, 1996. 4(2): p. 153-60.
3. Wellen, K. E. and G. S. Hotamisligil, Inflammation, stress, and diabetes. Journal of Clinical Investigation, 2005. 115(5): p. 1111-1119.
4. Grimble, R. F., Inflammatory status and insulin resistance. Curr Opin Clin Nutr Metab Care, 2002. 5(5): p. 551-9.
5. Anselmi, A., et al., Myocardial ischemia, stunning, inflammation, and apoptosis during cardiac surgery: a review of evidence. European Journal of Cardio-Thoracic Surgery, 2004. 25(3): p. 304-311.
6. Engler, R. L., G. W. Schmid-Schonbein, and R. S. Pavelec, Leukocyte capillary plugging in myocardial ischemia and reperfusion in the dog. American Journal of Pathology, 1983. 111(1): p. 98-111.
7. Entman, M. L., et al., Inflammation in the course of early myocardial ischemia. The FASEB journal, 1991. 5(11): p. 2529-2537.
8. Ross, R., Atherosclerosis—an inflammatory disease. New England Journal of Medicine, 1999. 340(2): p. 115.
9. Schmid-Schonbein, G. W., S. Takase, and J. J. Bergan, New advances in the understanding of the pathophysiology of chronic venous insufficiency. Angiology, 2001. 52(1): p. S27-34.
10. Suematsu, M., et al., The inflammatory aspect of the microcirculation in hypertension: oxidative stress, leukocytes/endothelial interaction, apoptosis. Microcirculation, 2002. 9(4): p. 259-276.
11. del Zoppo, G. J., Microvascular responses to cerebral ischemia/inflammation. Annals of the New York Academy of Sciences, 1997. 823(1): p. 132.
12. del Zoppo, G. J., et al., Polymorphonuclear leukocytes occlude capillaries following middle cerebral artery occlusion and reperfusion in baboons. Stroke, 1991. 22(10): p. 1276-1283.
13. Iadecola, C. and M. Alexander, Cerebral ischemia and inflammation. Curr Opin Neurol, 2001. 14(1): p. 89-94.
14. Jean, W. C., et al., Reperfusion injury after focal cerebral ischemia: the role of inflammation and the therapeutic horizon. Neurosurgery, 1998. 43(6): p. 1382-1396.
15. Kontos, C. D., et al., Cytochemical detection of superoxide in cerebral inflammation and ischemia in vivo. American Journal of Physiology—Heart and Circulatory Physiology, 1992. 263(4): p. 1234-1242.
16. Koistinaho, M. and J. Koistinaho, Interactions between Alzheimer's disease and cerebral ischemia-focus on inflammation. Brain Research Reviews, 2005. 48(2): p. 240-250.
17. Schmid-Schönbein, G. W., Analysis of inflammation. Annu Rev. Biomed. Eng., 2006. 8: p. 93-151.
18. Acosta, J. A., et al., Intraluminal pancreatic serine protease activity, mucosal permeability, and shock: a review. Shock, 2006. 26(1): p. 3-9.
19. Schmid-Schönbein, G. W., Mechanisms for cell activation and its consequences for biorheology and microcirculation: Multi-organ failure in shock. Biorheology, 2001. 38(2): p. 185-201.
20. Schmid-Schönbein, G. W., et al., Pancreatic enzymes and microvascular cell activation in multiorgan failure. Microcirculation, 2001. 8(1): p. 5-14.
21. Tierney, L. M., S. J. McPhee, and M. A. Papadakis, Current medical diagnosis & treatment. 2002: Lange Medical Books/McGraw-Hill.
22. DeLano, F. A. and G. W. Schmid-Schonbein, Protein-ase activity and receptor cleavage. Mechanism for insulin resistance in the spontaneously hypertensive rat: Hypertension 52 (2008), pp. 415-452
23. Lee, S. W., et al., Alterations in peripheral blood levels of TIMP-1, MMP-2, and MMP-9 in patients with type-2 diabetes. Diabetes Research and Clinical Practice, 2005. 69(2): p. 175-179.
24. Derosa, G., et al., Evaluation of metalloproteinase 2 and 9 levels and their inhibitors in diabetic and healthy subjects. Diabetes and Metabolism, 2007. 33(2): p. 129-134.
25. E. G. DelMar, C. Largman, J. W. Brodrick, M. C. Geokas, A sensitive new substrate for chymotrypsin, Anal. Biochem. 99 (1979) 316-320.
26. M. Zimmerman, B. Ashe, E. C. Yurewicz, G. Patel, Sensitive assays for trypsin, elastase, and chymotrypsin using new fluorogenic substrates, Anal. Biochem. 78 (1977) 47-51.
27. E. Anderson, K. W. C. Sze, S. K. Sathe, New colorimetric method for the detection and quantitation of proteolytic enzyme activity, J. Agric. Food Chem. 43 (1995) 1530-1534.
28. L. J. Jones, R. H. Upson, R. P. Haugland, N. Panchuk-Voloshina, M. Zhou, Quenched BODIPY dye-labeled casein substrates for the assay of protease activity by direct fluorescence measurement, Anal. Biochem. 251 (1997) 144-152.
29. D. Stockholm, M. Bartoli, G. Sillon, N. Bourg, J. Davoust, I. Richard, Imaging calpain protease activity by multiphoton FRET in living mice, J. Mol. Biol. 346 (2005) 215-222.
30. Y. Zhang, C. Haskins, M. Lopez-Cruzan, J. Zhang, V. E. Centonze, B. Herman, Detection of mitochondrial caspase activity in real time in situ in live cells, Microsc. Microanal. 10 (2004) 442-448.
31. L. M. Levine, M. L. Michener, M. V. Toth, B. C. Holwerda, Measurement of specific protease activity utilizing fluorescence polarization, Anal. Biochem. 247 (1997) 83-88.
32. S. Z. Schade, M. E. Jolley, B. J. Sarauer, L. G. Simonson, BODIPY-alpha-casein, a pH-independent protein substrate for protease assays using fluorescence polarization, Anal. Biochem. 243 (1996) 1-7.
33. D. E. Kleiner, W. G. Stetlerstevenson, Quantitative zymography: detection of picogram quantities of gelatinases, Anal. Biochem. 218 (1994) 325-329.

34. White, D., J. Stevens and J. Shultz, PepTag protease assay: a simple and rapid method for detection of very low amounts of protease, Promega Notes Magazine, 344, November 1993, p2.

35. U.S. Pat. No. 5,580,747, Dec. 3, 1996, J. W. Shultz and D. H. White

36. U.S. Pat. No. 6,942,778, Sep. 13, 2005, S. Jalali et al.

37. WO 2005/0666359 A1, Jul. 21, 2005, H. Sun et al

What is claimed is:

1. A peptide sequence comprising the sequence of any one of SEQ ID NOs: 4-6 and 11-13 or conservative amino acid substitutions thereof.

2. The peptide sequence of claim 1, wherein said sequence comprises a detectable moiety.

3. The peptide sequence of claim 2, wherein said detectable moiety is a fluorophore, a quantum dot, a fluorescent nanoparticle, a dendrimeric nanoparticle, a metallic nanoparticle, a chemiluminescent label, a electrochemical label or a oxidation/reduction label.

4. The peptide sequence of claim 3, wherein said detectable moiety is a fluorophore.

5. The peptide sequence of claim 3, wherein said detectable moiety is a chemiluminescent label.

\* \* \* \* \*